United States Patent
Theocharopoulos et al.

(10) Patent No.: US 9,856,165 B2
(45) Date of Patent: Jan. 2, 2018

(54) LEUCITE GLASS CERAMICS

(71) Applicant: Queen Mary and Westfield College University of London, London (GB)

(72) Inventors: Antonios Theocharopoulos, Cork (IE); Xiaohui Chen, Manchester (GB); Natalia Karpukhina, London (GB); Robert Hill, London (GB); Mike Cattell, London (GB)

(73) Assignee: Queen Mary and Westfield College University of London, London (GB)

( * ) Notice: Subject to any disclaimer, the term of this patent is extended or adjusted under 35 U.S.C. 154(b) by 0 days.

(21) Appl. No.: 14/901,120

(22) PCT Filed: Jun. 27, 2014

(86) PCT No.: PCT/EP2014/063775
§ 371 (c)(1),
(2) Date: Dec. 28, 2015

(87) PCT Pub. No.: WO2014/207244
PCT Pub. Date: Dec. 31, 2014

(65) Prior Publication Data
US 2016/0137547 A1      May 19, 2016

(30) Foreign Application Priority Data
Jun. 28, 2013   (GB) .................................. 1311663.7

(51) Int. Cl.
*C03C 10/10*   (2006.01)
*A61K 6/02*    (2006.01)
(Continued)

(52) U.S. Cl.
CPC .......... *C03C 10/0018* (2013.01); *A61K 6/026* (2013.01); *C03B 32/02* (2013.01);
(Continued)

(58) Field of Classification Search
CPC ............................ C03C 10/0018; A61K 6/026
See application file for complete search history.

(56) References Cited

U.S. PATENT DOCUMENTS

| 6,342,302 B1 | 1/2002 | Steidl et al. |
| 6,660,073 B1 * | 12/2003 | Panzera ................ C03C 4/0021 106/35 |

(Continued)

FOREIGN PATENT DOCUMENTS

| DE | 10351885 A1 | 5/2004 |
| EP | 0795311 A2 | 9/1997 |

(Continued)

OTHER PUBLICATIONS

Search Report for corresponding UK patent application No. GB1311663.7 dated Mar. 4, 2014.

(Continued)

*Primary Examiner* — Karl Group
(74) *Attorney, Agent, or Firm* — Renner, Otto, Boisselle & Sklar, LLP

(57) ABSTRACT

A leucite glass-ceramic is prepared from a glass comprising: about 66.8 to about 71.9 mol % of $SiO_2$, about 8.5 to about 10.6 mol % of $Al_2O_3$, about 9.5 to about 12.8 mol % of $K_2O$, about 0.5 to about 4.0 mol % of CaO, about 0 to about 3.0 mol % of $TiO_2$, about 1.8 to about 4.0 mol % of $Na_2O$, about 0.1 to about 6.0 mol % of $Li_2O$, about 0 to about 1.0 mol % of MgO, about 0 to about 3.0 mol % of $Nb_2O_5$, and about 0 to about 3.0 mol % of $B_2O_3$. The leucite glass-ceramic is prepared by subjecting the glass components to a nucleation heat treatment, followed by a growth heat treatment. The leucite glass-ceramic may be used in the fabrication of a Dental restoration using various processes, and may be used in the construction of Dental restorations such as ceramic Dental inlays, crowns, veneers, bridges, veneering materials (Continued)

for zirconium oxide restoration substrates, alumina oxide restoration substrates, or metal restoration substrates.

21 Claims, 13 Drawing Sheets

(51) Int. Cl.
    *C03C 10/00*     (2006.01)
    *C03B 32/02*     (2006.01)
    *C03C 3/087*     (2006.01)
    *C03C 3/091*     (2006.01)
    *C03C 4/00*     (2006.01)

(52) U.S. Cl.
    CPC .............. *C03C 3/087* (2013.01); *C03C 3/091* (2013.01); *C03C 4/0021* (2013.01); *C03C 10/0045* (2013.01); *C03C 10/0054* (2013.01)

(56) References Cited

U.S. PATENT DOCUMENTS 7,297,645 B2 * 11/2007 Krumbholz ............. C03C 3/097
                                                106/35

2004/0121894 A1    6/2004    Brodkin
2005/0034631 A1    2/2005    Conrad et al.
2005/0155518 A1 * 7/2005    Krumbholz ............. C03C 3/097
                                                106/35
2005/0277539 A1 * 12/2005    Assmann ............. A61K 6/0276
                                                501/6
2009/0081104 A1    3/2009    Ibsen et al.

FOREIGN PATENT DOCUMENTS

EP           1000588 A2      5/2000
EP           1329430      *    7/2003
EP           1435345 A2      7/2004
WO          99/45888         9/1999
WO          00/48956         8/2000

OTHER PUBLICATIONS

International Search Report and Written Opinion for corresponding patent application No. PCT/EP2014/063775 dated Oct. 29, 2014.

* cited by examiner

LEUCITE GLASS CERAMICS

This application is a national phase of International Application No. PCT/EP2014/063775 filed Jun. 27, 2014 and published in the English language.

FIELD OF THE INVENTION

The present invention relates to leucite glass-ceramics, and methods for their production of, in particular, translucent, high strength, leucite glass-ceramics for dental applications. The invention describes glasses where the thermal properties and refractive index are matched with the leucite crystal phase. The crystal morphology, volume fraction, and crystallization process may also be controlled in these formulations using different heat treatments and processing steps.

BACKGROUND OF THE INVENTION

Leucite glass-ceramics are extensively used in Dentistry to produce Dental prostheses including: Dental crowns, bridges, inlays, and veneers. These materials are particularly useful as they are biocompatible, highly aesthetic and can be fused, extruded, or machined into Dental restorations with ease. Such materials have also traditionally been fused to metal substrates and provided good clinical longevity over about 10 to 12 years.

There is an increased demand for all-ceramic restorations, which may increase further with the ageing population and the ever increasing use of adhesive dentistry.

However, all-ceramic restorations are still susceptible to brittle fracture (Kelly et al. J Prosthet Dent, 1996; 75:18-32), due to the presence of complex stress patterns during function and in areas of reduced ceramic thickness and being in a moist environment (Jones. Biocompatibility of Dental Materials, CRC Press Inc, 1982:81-96). Clinical failure rates for all-ceramic crowns are 52% (Burke and Lucarotti. J Dent, 2009, 37:12-24), and for porcelain veneers, failure rates are 47% (Burke and Lucarotti. J Dent, 2009, 37:31-38) over 10 years placed in the General Dental Service (cost of veneers=£6.2 million). This is unacceptably high and needs to be drastically improved.

Survival rates for leucite glass-ceramics are improved at 84.4% for posterior crowns after 11 years (Fradeani and Redemagni. Quintessence Int. 2002; 33:503-510).

Ceramic restorations when fused to metals have a lower failure rate of 38% Burke and Lucarotti. J Dent, 2009, 37:12-24) due to the reinforcement of the weak ceramic. Reinforcing weak porcelains with high strength metals or ceramic cores (zirconia) currently comes at high manufacturing cost and requires gross tooth reduction. Newer high strength zirconia and alumina core materials have been released on the market to address the all-ceramic strength issues. The opacity/hardness of these materials requires that they are veneered with aesthetic thermally compatible glasses which exhibit lower strengths than current leucite glass-ceramic materials. Failure of these materials at the core-veneer interface has subsequently been reported (Taskonak et al. Dent Mater, 2008; 24:1077-1082). Issues with the etching and long term adhesive bonding of fully crystalline zirconia core ceramics may also limit their applications (Walker et al., Dent Mater 2003; 19: 645-652). An overall thickness of 1.5-2 mm must be removed from the tooth surface in order to accommodate these bi- or tri-layer structures, which does not encourage the conservation of tooth structure.

The present development of leucite glass-ceramics which have a high area fraction of leucite fibers/particles and can combine high flexural strength together with good aesthetics is therefore useful in the field of Dentistry. These materials can be easily etched and adhesively bonded and used in situations of minimal tooth reduction.

Leucite glass-ceramics are typically produced via nucleation and crystal growth heat treatments of a glass. Typical commercial production methods produce dental glass-ceramics with 17 to 45% leucite content (Piche' et al., J Biomed Mater Res 1994; 28:603-9. Mackert et al., Int J Prosthodont, 1996; 9:261-265) with large leucite crystal sizes (~10 µm) and more irregular morphologies (Cattell et al., J Dent 1999; 27:183-96). The thermal expansion mismatch between the tetragonal leucite crystals and the glass matrix developed during leucite transformation can often cause signs of microcracking around larger non-uniform leucite crystals (Mackert et al., J Dent Res 1996; 75:1484-90), that has been linked to reduced mechanical properties (Shareef et al., 3 Mater Sci: Materials in medicine, 1994; 5:113-118. Cattell et al., Dent Mater 2001; 17:21-33). Current leucite glass-ceramic materials have low flexural strengths (120-140 MPa) and many of these materials have been linked to microstructural failure as reported in the literature. These materials can also have coarse microstructures that can wear the opposing teeth (Oh et al., J Prosthet Dent, 2002, 87:451-9.5, 6). This is another concern, as many patients grind their teeth at night which causes these materials to be more destructive to the opposing tooth surfaces.

The present invention seeks to design glasses which are thermally matched with the leucite crystal phase, preventing any glass matrix micro-cracking. This has led to a significant increase in the flexural strength (212-235 MPa) of these new materials compared to commercial materials. The refractive index of the glass and crystal phase is similarly matched in these new materials ensuring no loss of translucency. A high area fraction (>65%) of leucite crystals can therefore be produced and the morphologies controlled to give densely dispersed areas of orientated fibers, spheres, and rosette-shaped domains. In the present invention, solid state nuclear magnetic resonance spectroscopy has been used to find the optimal ratio between the glass and ceramic phase that delivers the highest strength of these new materials.

US 2005/0034631 A1 describes a high strength leucite glass-ceramic. However, this product is doped with zirconium oxide (60% by weight) and without such doping, the strength is only 107 MPa. Chemical curing is also employed to yield high strengths. These glasses also contain titanium dioxide in the base glass. The use of zirconium oxide is problematic in that it can cause opacity and may affect the translucency and aesthetics of the dental product. Given the high volume fractions of zirconium oxide present in the ceramics described in this publication, wear properties would be compromised since zirconia ceramics are known to suffer from low temperature degradation (J. R Kelly et al., Dent Mater 2008; 24:289-298). The use of chemical curing to achieve high strengths also adds to the manufacturing complexity and cost, and therefore should be avoided.

A high strength glass-ceramic described in WO 2009/073079 A1/WO 2009/038800 A1 benefits from a ball milling technique to produce the surface crystallization of leucite glass-ceramics. Without the ball milling of the glass powder, the biaxial flexural strength of this leucite glass-ceramic is only 153 MPa. This lengthy (4 hrs) ball milling procedure is problematic since it can induce zirconia contamination and additionally increases manufacturing time and cost. Furthermore, the process for producing the glass-ceramics of WO 2009/073079 A1/WO 2009/038800 A1 utilises a surface crystallization method, whereas it would be advantageous if leucite glass-ceramics were developed that could be crystallized by both a bulk and surface method. At present, bulk crystallization is rarely, if ever, reported for leucite glass-ceramics. In addition, the glass-ceramics of WO 2009/073079 A1/WO 2009/038800 A1 exclusively consist of round, ellipsoidal, crystals, whereas it would be advantageous if leucite glass-ceramics were developed that comprise a range of controllable morphologies including: leucite fibers, rosettes, and spheres. It would also be advantageous if the aspect ratio of the crystals could be varied in the said glass-ceramic via compositional changes.

U.S. Pat. No. 6,527,846 describes a high volume fraction leucite glass-ceramic with leucite crystals in needle or rod form with high flexural strength (200 MPa). No information is provided as to how to control the size of these crystals, or how to effect changes to the morphology by formulation or processing. It would be advantageous if leucite glass-ceramics were developed in which the morphology, area fraction, and refractive index could be controlled in order to influence the strength, thermal expansion, and aesthetics of the finished Dental restoration.

SUMMARY OF THE INVENTION

The present invention seeks to provide improved leucite glass-ceramics that overcome the problems associated with existing leucite glass-ceramics as described above. In particular, the present invention seeks to provide leucite glass-ceramics having one or more of the following properties: high flexural strength, high reliability, minimal microcracking, controlled translucency, controlled volume fraction of leucite crystals. The present invention achieves this by matching the refractive index of the glass-ceramic to the leucite phase, and/or matching the thermal properties of the glass-ceramic to the leucite phase.

Accordingly, the present invention describes the synthesis of Appen factor designed glasses which may be crystallized to produce leucite glass-ceramics with minimal microcracking, controlled translucency, and volume fraction of leucite crystals. These formulations can be produced with or without titanium dioxide or boric oxide as glass components. In some examples, either bulk or surface crystallization of the leucite can be utilized. The invention involves the copious nucleation and crystallization of leucite within the glass and control of its morphology. The leucite phase can be crystallised in orientated and densely dispersed areas of orientated fibers, spheres or rosette shaped domains. According to subtle changes in glass formulation, the morphology and aspect ratio of the fibers and crystal morphology may be altered with a subsequent increase in flexural strength and reliability.

In accordance with the present invention, there is provided a leucite glass-ceramic prepared from a glass comprising: about 66.8 to about 71.9 mol % of $SiO_2$, about 8.5 to about 10.6 mol % of $Al_2O_3$, about 9.5 to about 12.8 mol % of $K_2O$, about 0.5 to about 4.0 mol % of CaO, about 0 to about 3.0 mol % of $TiO_2$, about 1.8 to about 4.0 mol % of $Na_2O$, about 0.1 to about 6.0 mol % of $Li_2O$, about 0 to about 1.0 mol % of MgO, about 0 to about 3.0 mol % of $Nb_2O_5$, and about 0 to about 3.0 mol % of $B_2O_3$. The present invention also provides a leucite glass-ceramic prepared from a glass comprising: about 66.8 to about 71.9 mol % of $SiO_2$, about 8.5 to about 10.3 mol % of $Al_2O_3$, about 9.5 to about 12.8 mol % of $K_2O$, about 0.5 to about 4.0 mol % of CaO, about 0.0 to about 3.0 mol % of $TiO_2$, about 1.9 to about 4.0 mol % of $Na_2O$, about 0.1 to about 2.0 mol % of $Li_2O$, about 0 to about 1.0 mol % of MgO, about 0 to about 3.0 mol % of $Nb_2O_5$, and about 0 to about 3.0 mol % of $B_2O_3$.

The present invention also provides a method of preparing a leucite glass-ceramic of the invention comprising the steps of: (a) preparing a glass from the glass components specified above, and (b) subjecting the glass to a nucleation heat treatment followed by a growth heat treatment. Preferably, the nucleation heat treatment comprises heating at a temperature of about 587° C. to about 670° C. Preferably, the nucleation heat treatment is applied for a duration of about 0.5 hours to about 4 hours. Preferably, the growth heat treatment comprises heating at a temperature of about 795° C. to about 1075° C. Preferably, the growth heat treatment is applied for a duration of about 0.5 hours to about 3 hours.

Accordingly, the present invention also provides a method of preparing a leucite glass-ceramic of the invention comprising subjecting the glass components to a nucleation heat treatment at a temperature of about 587° C. to about 670° C. for a duration of about 0.5 hours to about 4 hours, followed by a growth heat treatment at a temperature of about 795° C. to about 1075° C. for a duration of about 0.5 hours to about 3 hours. The invention further provides a method of preparing a sanidine glass-ceramic or a leucite/sanidine glass-ceramic comprising subjecting the glass components to a nucleation heat treatment at a temperature of about 618° C. to about 620° C. for a duration of about 0.5 hours to about 4 hours, followed by a growth heat treatment at a temperature of about 720° C. to about 1075° C. for a duration of about 0.5 hours to about 3 hours.

A secondary processing heat treatment can also be utilised to transform the leucite fibers to a more spherical morphology. A further advantage of these glass-ceramics is the increased flexural strength (212.3-235 MPa) and reliability (m=19 for one formulation) after processing, compared with current leucite glass-ceramics available. The more homogeneous and fine crystal sizes produced may also be less destructive to the opposing tooth surfaces according to previous work (Theocharopoulos et al., IADR Abstract 3673:2010).

The present invention takes advantage of the modern technique of solid state nuclear magnetic resonance to follow up changes in the composition of the residual glass phase when the leucite phase crystallises. The result of the $^{27}Al$ NMR showed that the maximum strength in these new materials can be achieved when most of the aluminium present in the composition is consumed by the crystallising leucite phase and amount of aluminium in the residual glass phase is minimised. The refractive index of the present glass formulations is controlled using Appen factor predictions to produce a similar refractive index (R.I.) to the leucite crystals (R.I.=1.510, Deer et al., 2004, Rock forming minerals, 304-315) even at high leucite volume fractions.

Translucent high strength and reliable leucite glass-ceramics are therefore the outcome of the present invention and can be used to fabricate dental restorations using sintering, heat pressing or CAD-CAM technology. The microstructural-mechanical properties of these ceramics may be tailored to suit the method of manufacture or clinical usage. That is, the crown substrate material can be produced so that it has crystal morphology with a higher aspect ratio and a high flexural strength to resist chipping or fracture. A more spherical or mixed leucite morphology with high strength can also be produced for a veneering material to avoid tooth destruction through tooth wear.

BRIEF DESCRIPTION OF THE FIGURES

FIG. 3 shows the $^{27}$Al triple-quantum MAS NMR spectrum of the glass-ceramic of Example 1a.

DETAILED DESCRIPTION OF THE INVENTION

Figure 1:
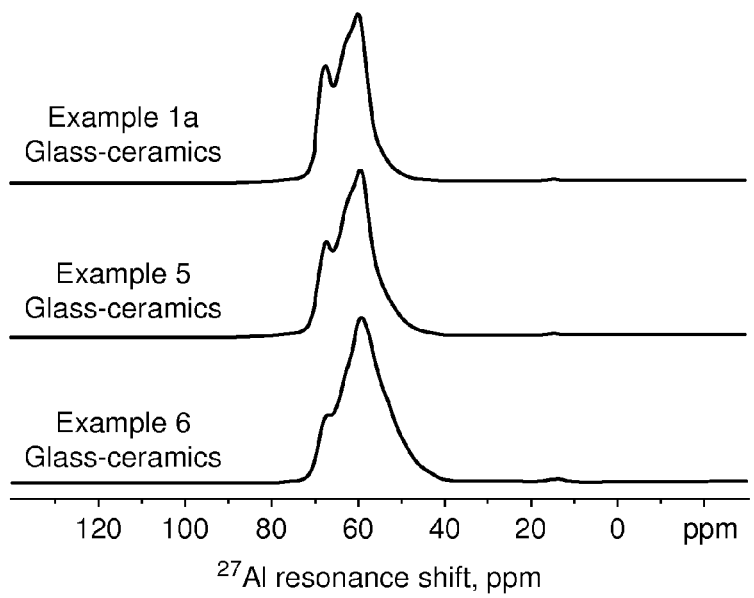
FIG. 1 shows the $^{27}$Al MAS NMR spectra for glass-ceramics of the invention.

The present invention provides a leucite glass-ceramics with high flexural strength, high reliability, minimal micro-cracking, controlled translucency, and/or controlled volume fraction of leucite crystals, the properties being achieved by matching the refractive index of the glass-ceramic to the leucite phase, and/or matching the thermal properties of the glass-ceramic to the leucite phase.

The following definitions shall apply throughout the specification and the appended claims.

Within the context of the present specification, the term "comprises" is taken to mean "includes" or "contains", i.e. other integers or features may be present, whereas the term "consists of" is taken to mean "consists exclusively of".

Within the present specification, the term "about" means plus or minus 20%; more preferably plus or minus 10%; even more preferably plus or minus 5%; most preferably plus or minus 2%.

The present invention employs a novel strategy for developing leucite glass-ceramics with particularly advantageous properties through the use of Appen factors to predict the glass properties using the following equation:

$$\alpha = \alpha_1 p_1 + \alpha_2 p_2 + \ldots + \alpha_n p_n = \sum_{i=1}^{n} \alpha_i p_i$$

where ai indicates the properties contribution of each oxide to glass, and Pi is the weight fraction of each oxide.

The various properties (density, thermal expansion coefficient, refractive indices, fusion temperature) for each of the oxide components for use in the above Appen factor equation are as follows:

| | Appen Factors | | | |
|---|---|---|---|---|
| Oxide component | Density $p_i$ (g/cm$^3$) | Thermal Expansion Coefficient (TEC) (×10$^{-6}$/K, 20-400° C.) | Refractive Index (R.I.) $n_i$ | Fusion Temperature (° C., Winkelmann and Schott) |
| SiO$_2$ | 26.1-27.25 | 0.5-3.8 | 1.4585-1.475 | 6.161 |
| Al$_2$O$_3$ | 40.4 | −3.0 | 1.520 | 34.585 |
| K$_2$O | 34.1 (33.5) | 46.5 (42.0) | 1.575 (1.595) | 783.92 |
| CaO | 14.4 | 13.0 | 1.730 | 885.046 |
| TiO$_2$ | 20.5 | −1.5-3.0 | 2.080-2.230 | −79.806 |
| Na$_2$O | 20.2 | 39.5 | 1.590 | 670.233 |
| Li$_2$O | 11.0 | 27.0 | 1.695 | |
| MgO | 12.5 | 6.0 | 1.610 | 1125.698 |

For some Appen Factors, the following remarks apply:
SiO$_2$: when $67 \leq p_{SiO_2} \leq 100$,
$\alpha_{SiO_2} = 10.5 - 0.1 \cdot p_{SiO_2}$, $\rho_{SiO_2} = 23.75 + 0.035 \cdot p_{SiO_2}$ and $n_{SiO_2} = 1.5085 - 0.0005 \cdot n_{SiO_2}$,
when $p_{SiO_2} \leq 67$, $\rho_{SiO_2} = 26.1$, $\alpha_{SiO_2} = 3.8$, and $n_{SiO_2} = 1.475$.
K$_2$O: the values in parentheses only apply to glass with composition of $p_{Na_2O} < 1\%$,
TiO$_2$: when $50 \leq p_{SiO_2} \leq 80$, $\alpha_{TiO_2} = 10.5 - 0.15 \cdot p_{SiO_2}$ and $\alpha_{TiO_2} = 2.480 - 0.005 \cdot p_{SiO_2}$.

The weight percentage of oxides $p_i$ is expressed in mole percentage (Scholze and Lakin, 1991).

Using the glass prediction results, a range of glasses was designed using glass reagents with compositions listed in Table IA in the form of silicates, carbonates and oxides.

TABLE IA

| Materials | Mole Percentage |
|---|---|
| $SiO_2$ | 66.8-71.9 |
| $Al_2O_3$ | 8.5-10.6 |
| $K_2O$ | 9.5-12.8 |
| CaO | 0.5-4.0 |
| $TiO_2$ | 0-3.0 |
| $Na_2O$ | 1.8-4.0 |
| $Li_2O$ | 0.1-6.0 |
| MgO | 0-1.0 |
| $Nb_2O_5$ | 0-3.0 |
| $B_2O_3$ | 0-3.0 |

Accordingly, the present invention provides a leucite glass-ceramic prepared from a glass comprising: about 66.8 to about 71.9 mol % of $SiO_2$, about 8.5 to about 10.6 mol % of $Al_2O_3$, about 9.5 to about 12.8 mol % of $K_2O$, about 0.5 to about 4.0 mol % of CaO, about 0 to about 3.0 mol % of $TiO_2$, about 1.8 to about 4.0 mol % of $Na_2O$, about 0.1 to about 6.0 mol % of $Li_2O$, about 0 to about 1.0 mol % of MgO, about 0 to about 3.0 mol % of $Nb_2O_5$, and about 0 to about 3.0 mol % of $B_2O_3$.

Using the glass prediction results, another range of glasses were designed using glass reagents with compositions listed in Table IB in the form of silicates, carbonates and oxides.

TABLE IB

| Materials | Mole Percentage |
|---|---|
| $SiO_2$ | 66.8-71.9 |
| $Al_2O_3$ | 8.5-10.3 |
| $K_2O$ | 9.5-12.8 |
| CaO | 0.5-4.0 |
| $TiO_2$ | 0-3.0 |
| $Na_2O$ | 1.9-4.0 |
| $Li_2O$ | 0.1-2.0 |
| MgO | 0-1.0 |
| $Nb_2O_5$ | 0-3.0 |
| $B_2O_3$ | 0-3.0 |

Accordingly, the present invention also provides a leucite glass-ceramic prepared from a glass comprising: about 66.8 to about 71.9 mol % of $SiO_2$, about 8.5 to about 10.3 mol % of $Al_2O_3$, about 9.5 to about 12.8 mol % of $K_2O$, about 0.5 to about 4.0 mol % of CaO, about 0 to about 3.0 mol % of $TiO_2$, about 1.9 to about 4.0 mol % of $Na_2O$, about 0.1 to about 2.0 mol % of $Li_2O$, about 0 to about 1.0 mol % of MgO, about 0 to about 3.0 mol % of $Nb_2O_5$, and about 0 to about 3.0 mol % of $B_2O_3$.

It has surprisingly been found that the $K_2O$ content has an effect on the morphology of the crystals. Higher contents of $K_2O$ tend to result in glass-ceramics with higher proportions of spherical crystals which are useful in certain applications. Accordingly, in one embodiment, the $K_2O$ content is from about 10.0 to about 12.8 mol % Lower contents of $K_2O$ tend to result in glass-ceramics with higher proportions of crystals in the form of elongated fibers, which have a number of advantages in terms of strength and machinability in certain applications. Accordingly, in another embodiment, the $K_2O$ content is from about 9.5 to about 10.0 mol %.

In a preferred embodiment of the invention, the CaO content is from about 0.5 to about 3.0 mol %.

It has surprisingly been found that the leucite glass-ceramics of the present invention can be produced with or without titanium dioxide nucleating agents. Previously, it was thought that the presence of titanium dioxide was essential for effective crystallization of leucite to occur. Accordingly, in one embodiment of the invention, the $TiO_2$ content is less than about 0.1 mol %; more preferably, no titanium dioxide is used.

In one preferred embodiment of the invention, the $Li_2O$ content is from about 0.1 to about 2.0 mol %. In a more preferred embodiment of the invention, the $Li_2O$ content is from about 0.1 to about 1.6 mol %.

In an alternative preferred embodiment of the invention, the $Li_2O$ content is from about 1.6 mol % to about 6.0 mol %; more preferably, from about 2.0 mol % to about 4.0 mol %; most preferably, from about 2.0 mol % to about 6.0 mol %. It has surprisingly been found that utilising a higher percentage of $Li_2O$ results in a lowering of the temperature of manufacture, resulting in lower manufacturing costs, improved ease of manufacturing, and reduced safety risks of manufacturing.

In a preferred embodiment of the invention, the MgO content is from about 0 to about 0.5 mol %. More preferably, the MgO content is from about 0.1 to about 0.5 mol %. In a preferred embodiment of the invention, the $Nb_2O_5$ content is from about 0.5 to about 2.0 mol %.

It has surprisingly been found that the leucite glass-ceramics of the present invention can be produced with or without boric oxide as a glass component, whereas it was previously considered that this was an essential component for producing leucite glass-ceramics. Accordingly, in one embodiment of the invention, the $B_2O_3$ content is less than about 0.1 mol %; more preferably, no boric oxide is used.

It has surprisingly been found that the calcium oxide and titanium dioxide components have a synergistic effect when used in approximately equal molar percentages. Leucite glass-ceramics prepared from glasses comprising approximately equal molar percentages of calcium oxide and titanium dioxide have been shown to produce tetragonal leucite glass-ceramics with high reliability, and with varying microstructures. Accordingly, in one embodiment of the invention, the glass-ceramic is prepared from a glass comprising approximately equal molar percentages of CaO and $TiO_2$. In this embodiment, the CaO content is preferably from about 0.5 to about 3.0 mol %, and the $TiO_2$ content is preferably from about 0.5 to about 3.0 mol %.

Glasses were designed to attain thermal expansion coefficients ranging from about $8.5 \times 10^{-6}/K$ to about $10.7 \times 10^{-6}/K$ (Table II) and with calculated refractive indices (RI) similar to the leucite phase (natural leucite RI=1.508-1.511). Accordingly, in one embodiment of the invention, the leucite glass-ceramic has a refractive index that is matched to the leucite phase and/or the leucite glass-ceramic has thermal properties that are matched to the leucite phase. In another embodiment of the invention, the leucite glass-ceramic displays one or more of the following properties: (1) a leucite area fraction of from about 33.1 to about 65.7%; (2) a glass coefficient of thermal expansion (CTE) of from about $8.5 \times 10^{-6}/K$ to about $10.7 \times 10^{-6}/K$ at 100-400° C.; and (3) a glass-ceramic coefficient of thermal expansion (CTE) of from about $15.7 \times 10^{-6}/K$ to about $24.9 \times 10^{-6}/K$ at 100-400° C. Preferably, the refractive index of the leucite glass-ceramic is such that the glass-ceramic being translucent.

The fusion temperature contribution of each oxide (Winkelmann and Schott, 1894) was also taken into account to provide an estimate of the likely processing temperatures available. Processing temperatures were calculated to ensure they were in the range suitable for dental restoration manufacturing parameters.

It has been found by the present inventors that high flexural strength (i.e. at least about 200 MPa) is achieved when the maximum aluminium present in the novel glass composition is consumed by the crystallising leucite phase and minimum aluminium remains in the glass matrix. Accordingly, in one embodiment of the invention, the leucite glass-ceramic displays high flexural strength of at least about 200 MPa.

Leucite glass-ceramics of the present invention provide a range of controllable morphologies which may be useful for different specific applications. Accordingly, in one embodiment of the invention, the morphology of the crystals of the leucite glass-ceramic is mainly in the form of fibers, rosettes, and/or spheres.

Leucite glass-ceramics of the present invention may be prepared by any suitable method known to the skilled person.

In one embodiment of the invention, there is provided a method of preparing a leucite glass-ceramic of the invention comprising the steps of: (a) preparing a glass from the glass components specified above, and (b) subjecting the glass to a nucleation heat treatment followed by a growth heat treatment. Preferably, the nucleation heat treatment comprises heating at a temperature of about 587° C. to about 670° C. Preferably, the nucleation heat treatment is applied for a duration of about 0.5 hours to about 4 hours. Preferably, the growth heat treatment comprises heating at a temperature of about 795° C. to about 1075° C. Preferably, the growth heat treatment is applied for a duration of about 0.5 hours to about 3 hours.

In a further embodiment of the invention, there is provided a method of preparing a leucite glass-ceramic of the invention comprising subjecting the glass components to a nucleation heat treatment at a temperature of about 587° C. to about 670° C. for a duration of about 0.5 hours to about 4 hours, followed by a growth heat treatment at a temperature of about 795° C. to about 1075° C. for a duration of about 0.5 hours to about 3 hours. Using such a method, the leucite glass-ceramic may be crystallised via a bulk crystallisation mechanism or via a surface crystallisation mechanism.

In another embodiment of the invention, there is provided a method of preparing a sanidine glass-ceramic or a leucite/sanidine glass-ceramic comprising subjecting the glass components as defined above to a nucleation heat treatment at a temperature of about 618° C. to about 620° C. for a duration of about 0.5 hours to about 4 hours, followed by a growth heat treatment at a temperature of about 720° C. to about 1075° C. for a duration of about 0.5 hours to about 3 hours.

In order to prepare the leucite glass-ceramics of the invention, one specific procedure will now be described with reference to the Examples below. Raw materials are melted in an electrical chamber furnace (UAF1600 furnace, Lenton, Hope Valley, UK) at 1550° C. for about 5-6 hours (composition dependant, see Examples for representative conditions). Glass melts are next annealed at 500° C. for about 1 hour in a preheated furnace (Tris Burnout furnace, Dentalfarm, Italy), followed by furnace cooling. After cooling, the glass frits may be ball milled and sieved through a 125 micron sieve. In order to refine the microstructure, glasses may be remelted for about 2 hours at 1400-1550° C., and then annealed for about 2 hours at 500° C., reground, and then sieved through a 125 micron sieve. Glasses prepared using the method as described in the Examples below were transparent.

Leucite glass-ceramics are produced by using a two-step heat treatment in all instances. Glass powders are heated in an electric furnace (RHF 1600, Carbolite, Bamford, UK) using different nucleation and crystal growth temperatures and holds (representative conditions are described in Examples 1-8). After the heat treatment, the glass-ceramics are air quenched. The glass frits are crushed and ground in a ball mill (Pascall Engineering ltd, UK) for about 2 hours then screened using a 125 µm sieve.

The area fraction and morphology of the leucite crystals can be controlled in the glass-ceramics of the invention depending on the composition and type of heat treatment applied (various representative conditions being described in Examples 1-8). It is possible to crystallise a high area fraction (>65%) of elongated fiber-like leucite crystals with high aspect ratio (as shown in Example 1), together with a high density of more spherical crystals. These elongated fiber-like crystals grow in preferred orientated domains. Re-homogenisation of these glasses can refine these crystallites (as demonstrated in Example 1, and FIG. 5). Leucite glass-ceramics are generally accepted as surface nucleated. A bulk or a surface crystallization process (depending on the formulation) can be taken advantage of in order to affect the microstructure, in terms of changes to the crystal morphology and/or area fraction. The leucite glass-ceramics of the invention can also be produced without titanium dioxide as a nucleating agent (as demonstrated in Example 3), whereas titanium dioxide was previously considered essential for the copious crystallization of leucite.

The addition of $TiO_2$ and CaO of equal molar % to a base formulation (as demonstrated in Examples 2, 2a, 2b, and 2c) can, however, be used to change the leucite morphology (crystallite aspect ratio) with an increase in strength (to about 224-234 MPa) and reliability (m=18.9). These values for reliability are higher than that found for traditional dental ceramics (Cattell et al., 1997, J Dent, 25; 409-414). These glass-ceramics attained a high coefficient of thermal expansion (19.6-24.9) with no glass matrix microcracking (as demonstrated in Example 2, 2a, 2b, 2c) which is linked to the improved mechanical performance.

A structural factor linked to mechanical performance and evaluated via solid state nuclear magnetic resonance relates to the amount of aluminium remaining in the glass matrix after crystallization of leucite. To achieve high strength in the materials of the present invention, it is desirable to maximize consumption of aluminium by the leucite phase and minimize residual aluminium in the glass matrix as shown by $^{27}Al$ magic angle spinning nuclear magnetic resonance (MAS NMR). FIG. 1 shows $^{27}Al$ MAS NMR spectra for representative leucite glass-ceramics of the invention (Examples 1a, 5 and 6). The spectrum for the leucite glass-ceramic of Example 1a shows maximum consumption of aluminium into the leucite phase, with minimum aluminium remaining in the glass matrix.

Figure 4:
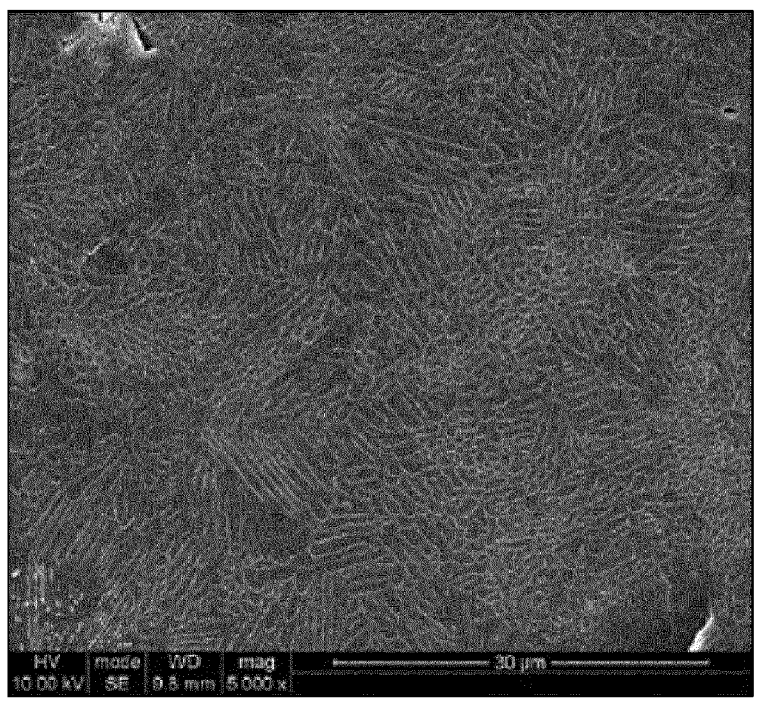
FIG. 4 shows the SEM photomicrograph images of the glass-ceramic of Example 1 with orientated fiber-like crystals.
Figure 5:
FIG. 5 shows the SEM photomicrograph images of the re-homogenized glass-ceramic of Example 1a with fine leucite fibers (refined microstructure).
Figure 6:
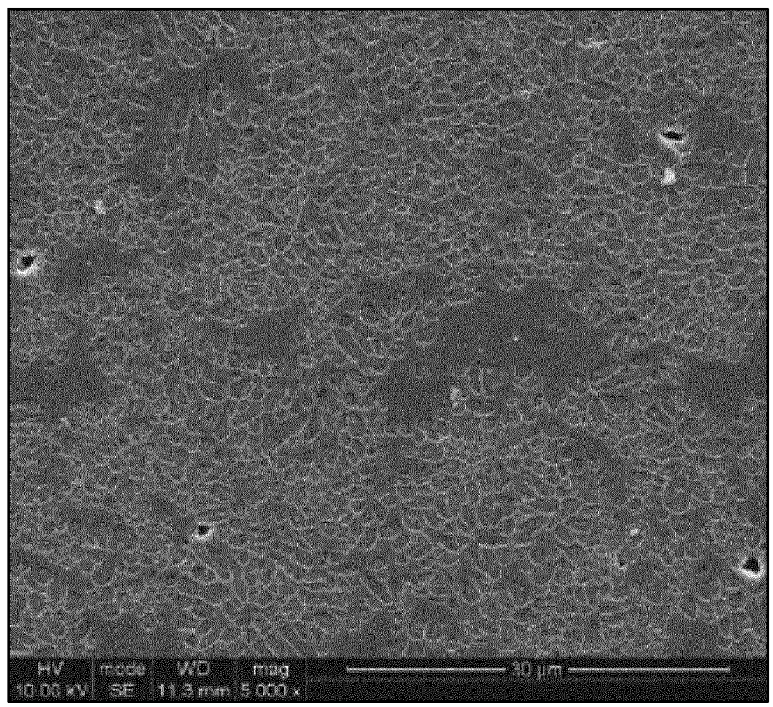
FIG. 6 shows the SEM photomicrograph of the re-homogenized glass-ceramic of Example 1a after a secondary heat treatment showing ripening of the leucite crystals.

The degree of crystallization and crystal morphology can also be varied according to the crystallization heat treatment selection. The present invention provides leucite glass-ceramics with fibers, spherical or mixed morphologies, with resultant changes in the mechanical properties as is presented in Examples 1-8 (Table IV). It is also possible to change the microstructure of some of these glass-ceramic formulations by a short secondary processing heat treatment to produce a dense dispersal of more spherical type crystals (as demonstrated in Examples 1 and 1a) and a ripening of the leucite growth (as demonstrated in Example 1a). No microcracking was present in the glassy matrix of many of the Example leucite glass-ceramics of the present invention (as shown in FIGS. 4, 5 and 6) and a high flexural strength is produced (212.3±28 MPa, Table IV).

Process for Producing Dental Restorations

The leucite glass-ceramics of the present invention find particular application in the field of dentistry, and in particular, in the fabrication of dental restorations, such as inlays, crowns, veneers, bridges, and veneering materials for other restoration substrates.

Accordingly, the present invention provides for the use of a leucite glass-ceramic of the invention or a sanidine glass-ceramic or a leucite/sanidine glass-ceramic prepared by the method of the invention in the construction of a Dental restoration selected from the group consisting of a ceramic Dental inlay, a crown, a veneer, a bridge, and a veneering material for a zirconium oxide restoration substrate, an alumina oxide restoration substrate, or a metal restoration substrate.

The present invention also provides a Dental restoration selected from the group consisting of: a ceramic Dental inlay, a crown, a veneer, a bridge, and a veneering material for a zirconium oxide restoration substrate, an alumina oxide restoration substrate, or a metal restoration substrate, comprising a leucite glass-ceramic of the invention or a sanidine glass-ceramic or a leucite/sanidine glass-ceramic prepared by the method of the invention.

Fabrication of dental restorations of the present invention can be via several routes.

The glass-ceramic materials can be sintered and glazed on a refractory cast in a vacuum oven. The refractory may then be removed and the restoration etched before adhesive bonding in the dental surgery.

Alternatively, the glasses or glass-ceramic powders can be transferred to a special made steel die and compacted under pressure to produce powder or sintered ingots. These ingots may be extruded into refractory moulds using a heat extrusion technique at temperatures of between about 1000 and about 1150° C., using a 10 minute hold and 15 minutes under pressure. A suitable technique is described in EP 231 773. After removal of the refractory material, the glass-ceramic can next be coloured using stains and glazing in a vacuum oven. Alternatively, the glass-ceramic may be cut back and veneered with a sintered ceramic to further characterise the aesthetics.

The glass-ceramics of the present invention may also be utilised for computer aided design and computer aided manufacturing techniques (CAD-CAM). Glass-ceramic powders may be formed into blanks using heat extrusion or powder compaction and sintering. The morphology and volume fraction of the glass-ceramic of the present invention for use in this technique can be carefully controlled using the processes described herein to allow accurate machining of the dental restoration and to avoid chipping. These blanks may be machined to the desired geometry at the chair side or in the laboratory using currently available CAD-CAM technology. The machined restoration is next stained and glazed in a dental oven/furnace. The glass-ceramics of the present invention may also be printed using 3D printing and using selective binders including: polylactic acid, polymeric additives, sucrose, starch or inorganic binder solutions, followed by sintering in a dental oven/furnace.

Accordingly, the present invention also provides for the use of a leucite glass-ceramic of the invention or a sanidine glass-ceramic or a leucite/sanidine glass-ceramic prepared by the method of the invention in the fabrication of a Dental restoration using one or more of the following processes: sintering, heat pressing, Computer-Aided Design/Computer-Aided Manufacturing (CAD/CAM) technology, and 3D printing technology.

Embodiments have been described herein in a concise way. It should be appreciated that features of these embodiments may be variously separated or combined within the invention.

EXAMPLES

Example 1

Glass batches consisted of the following components (mole %): $SiO_2$, 69.3%; $Al_2O_3$, 10.1%; $K_2O$, 12.5%; CaO, 2.1%; $TiO_2$, 0.5%; $Na_2O$, 4.0%; $LiO_2$, 1.1%; MgO, 0.5%.

The components were mixed on a jar roll for 2 hours. The batch was transferred to a 90% Pt-10% Rh crucible and heated in an electrical chamber furnace (UAF1600 furnace, Lenton, Hope Valley, UK) at a rate 10° C./min up to 1550° C. and held for 5 hours. The glass was next transferred into an annealing furnace (Tris Burnout furnace, Dentalfarm, Italy) at 500° C. for 2 hours, and then cooled to room temperature. The glass frits were crushed and ground in a ball mill (Pascall Engineering ltd, UK) for 2 hours then screened using a 125 μm sieve. One batch of the ground glass was re-homogenised (Example 1a) by a further heating for 2 hours at 1400° C. and then annealed again as previously for 2 hours at 500° C. The glass frit was then re-ground and sieved through a 125 micron sieve. All glasses prepared were clear and transparent. X-ray diffraction was carried out on the glasses using a Siemens D5000 X-ray diffractometer using flat plate geometry. Graphite monochromated Cu Kα radiation ($\lambda 1=1.54056$ Å and $\lambda 2=1.54439$ Å) was used. Data were collected from 5 to 110° two-theta, with a step size 0.02° and a count time of 12 seconds. Glass samples were confirmed as amorphous and leucite free.

Figure 2:
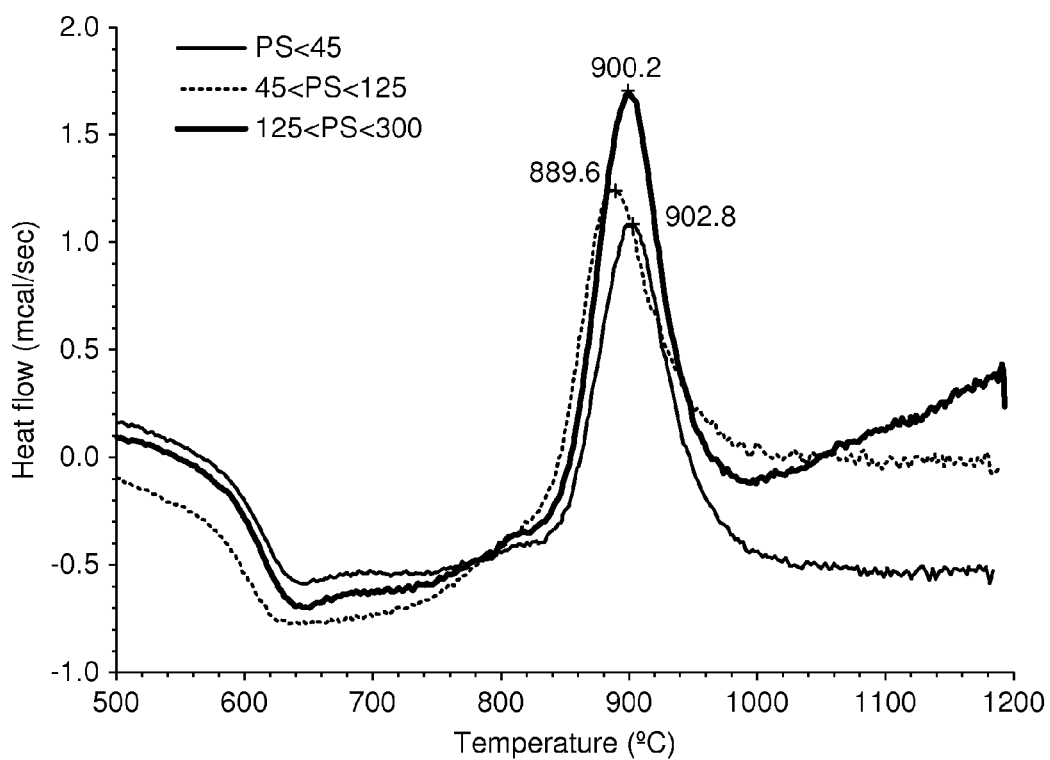
FIG. 2 shows the DSC traces of the glass of Example 1 at a rate of 20° C./minute.

The present glasses were explored using Differential Scanning calorimetry (DSC) and the crystallization peak was not sensitive to particle size indicating a bulk crystallization mechanism (FIG. 2). Surface crystallisation was previously thought to be largely responsible for the crystallisation of leucite in aluminosilicate glasses (Höland et al., J Non-Cryst Solids 450 1995; 180: 292-307.25). High speed planetary milling (Pulverisette P7, Fritsch, Idar-Oberstein, Germany) of the glass (0.5-1 hour) to effect surface crystallisation did not lead to an increased number of crystallites. Increase in crystallite number and reduction in median size was achieved after 2 hours high speed milling and may be associated with a change in crystallisation mechanism, but did not translate to increased flexural strengths (192.5±44 MPa Table III). Fine crystallite size is associated with reduced enamel wear in leucite glass-ceramics and this describes a route to achieve a low wear veneer material via this milling process and change in crystallisation mechanism.

To produce the glass-ceramics, the glasses were heat treated in an electric furnace (RHF 1600, Carbolite, Bamford, UK) using two-step heat treatments. In one embodiment, the un-homogenised glass was heated at a rate of 10° C./min to 610° C. and held for 1 hour, wherein allows the nucleation of leucite; and then ramped to 870° C. and held for 1 hour hold (Example 1, FIG. 4). After heat treatments the glass-ceramic was rapidly air quenched. This produced orientated domains of fiber like crystals in the glassy matrix and a mean (SD) biaxial flexural strength of 199.3 (20.6) MPa (Table IV). Following re-melting (re-homogenisation) of the glass and using the same nucleation and growth temperatures, it was possible to change the microstructure to rosette shaped domains of orientated leucite fibers and a high density of spherical leucite crystals in the glassy matrix (>65% area fraction leucite).

Figure 3:
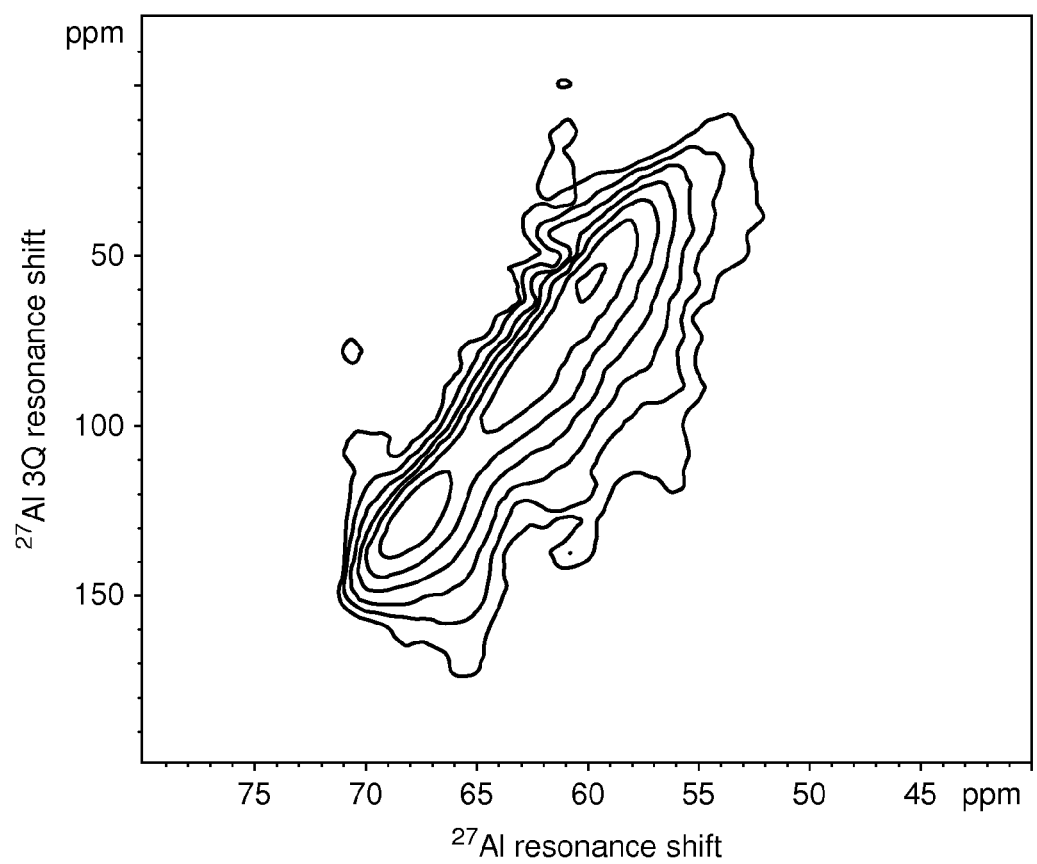

Another embodiment was heat treatment of the re-homogenised glass, wherein the glass was heated at a rate of 20° C./min to 620° C. (or to 591° C.) and held for 1 hour hold, and then ramped to 795° C. and held for 1 hour (or held for 30 mins), followed by air quenching (Example 1a, FIG. 5). A high area fraction of elongated leucite crystals with high aspect ratio together with a high density of fine spherical crystals were crystallized. The elongated fiber-like crystals tend to grow in a preferred manner and form orientated domains. Re-homogenised glasses yielded a much finer microstructure (FIG. 5), which also contained some rosette shaped orientated domains mentioned earlier. These glass-ceramics have high TEC values (19.7 to 21×10−6/K at 100-400° C., Table III), especially at the higher temperature range (400-600° C.) which is around 30×10-6/K. This indicates the high leucite volume fraction of the glass-ceramics, which in agreement with the secondary electron microscope images. All glass-ceramics were confirmed as tetragonal leucite according to high and low temperature XRD data. Additionally, the $^{27}Al$ triple-quantum magic angle spinning nuclear magnetic resonance experiment has been run for the glass-ceramics (Example 1a). The resulting spectrum in FIG. 3 shows three distinct aluminium sites typical for the leucite phase (Baltisberger et al., J Am Chem Soc 1996; 118: 7209-7214).

It is also possible to change the microstructure of the present glass-ceramics by a short secondary heat treatment to produce a dense dispersal of more spherical type crystals (FIG. 6). The glass-ceramic frit is first ball milled and sieved through a 125 micron sieve to produce glass powder. The powders are vacuum sintered in a dental furnace respectively using a heating rate of 38° C./min. The re-homogenised glass-ceramic specimens were sintered at 1100° C. for 2 mins (FIG. 6). All the sintered specimens showed a high degree of translucency. No microcracking was present in the glassy matrix of the glass-ceramics and the ability to change the microstructure was demonstrated. A high Mean (SD) biaxial flexural strength was produced for this glass-ceramic formulation of 212.3 (28) MPa, Table IV).

Figure 7:
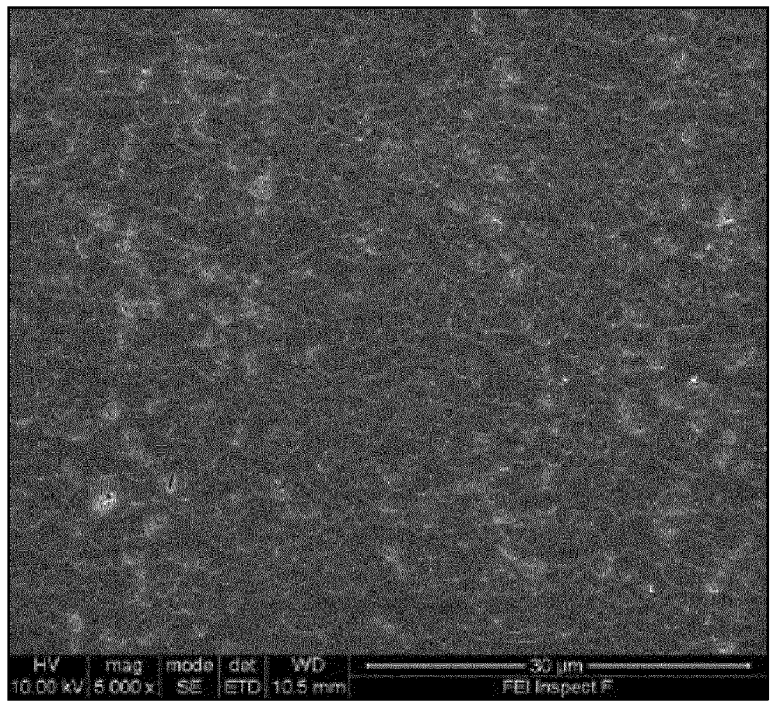
FIG. 7 shows the SEM photomicrograph of the re-homogenized glass-ceramic of Example 1a after heat extrusion.

In order to induce uniformity of microstructure in the said glass-ceramics, it can be heat extruded. Glass-ceramic powders were transferred to a steel die and compacted under pressure to produce powder or sintered ingots. These ingots may be extruded into refractory moulds using a heat extrusion technique at temperatures of between 1000 and 1150° C., using a 10 min hold and 15 min under pressure. This technique is described in EP 231 773. During this process, the crystals are deliberately grown and the crystal morphology controlled to produce a dense dispersal of uniformly distributed crystals. This eliminates any areas of glassy matrix that may be susceptible to microcracking (FIG. 7). Microcracking is also restricted to the leucite crystals ensuring a strong composite structure which is less likely to fracture and wear the opposing tooth structure. A translucent (refractive index=1.510) and processable glass-ceramic for dental applications is therefore produced. Heat extrusion led to a high Mean (SD) biaxial flexural strength of 227 (35.2) MPa (Table IV). Higher values for reliability (m=11.9) were also achieved by using different glass heat treatments (e.g. 620° C. for a 1-hour hold or 795° C. for a 1 hour-hold) prior to ingot fabrication.

Example 2

Glass reagents batched in the form of silicates, carbonates and oxides consisted of the following components (Mole %):

Example 2

$SiO_2$, 70.4%; $Al_2O_3$, 10.3%; $K_2O$, 12.7%; CaO, 0.5%; $TiO_2$, 0.5%; $Na_2O$, 4.0%; $LiO_2$, 1.1%; MgO, 0.5%.

Example 2a $SiO_2$, 69.6%; $Al_2O_3$, 10.2%; $K_2O$, 12.5%; CaO, 1.0%; $TiO_2$, 1.0%; $Na_2O$, 4.0%; $LiO_2$, 1.1%; MgO, 0.5%.

Example 2b $SiO_2$, 68.2%; $Al_2O_3$, 10.0%; $K_2O$, 12.3%; CaO, 2.0%; $TiO_2$, 2.0%; $Na_2O$, 3.9%; $LiO_2$, 1.1%; MgO, 0.5%.

Example 2c $SiO_2$, 66.8%; $Al_2O_3$, 9.7%; $K_2O$, 12.0%; CaO, 3.0%; $TiO_2$, 3.0%; $Na_2O$, 3.8%; $LiO_2$, 1.1%; MgO, 0.5%.

The components were mixed on a jar roll for 2 hours. The batch was transferred to an 90% Pt-10% Rh crucible and heated in an electrical chamber furnace (UAF1600 furnace, Lenton, Hope Valley, UK) at a rate 10° C./min up to 1550° C. and held for 5 hours. The glass melt was next transferred into an annealing furnace (Tris Burnout furnace, Dentalfarm, Italy) operating at 500° C. for 2 hours, and then slowly cooled down to room temperature. The glass frits were crushed and ground in a ball mill (Pascall Engineering ltd, UK) for 2 hours then screened using a 125 µm sieve. The glass powders were re-homogenised by remelting for 2 hours at 1550° C., and annealed for 2 hours at 500° C. and furnace cooled to room temperature. The glass frit was then re-ground and sieved through a 125 micron sieve. All glasses prepared were transparent. X-ray diffraction was carried out on the glasses using a Siemens D5000 X-ray diffractometer using flat plate geometry. Graphite monochromated Cu Kα radiation (λ1=1.54056 Å and λ2=1.54439 Å) was used. Data was collected from 5 to 110° two-theta, with a step size 0.02° and a count time of 12 seconds. Glass samples were confirmed as amorphous.

Figure 8:
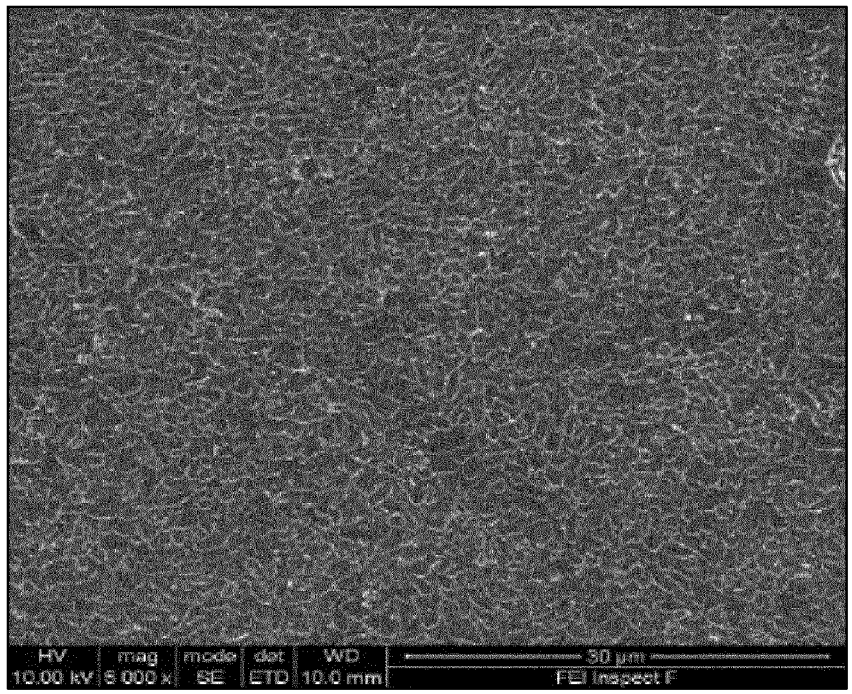
FIG. 8 shows the SEM photomicrograph of the glass-ceramic of Example 2a showing a uniform microstructure of largely rounded leucite crystals.

In order to crystallise the glass-ceramics the glass powders were heat treated in an electric furnace (RHF 1600, Carbolite, Bamford, UK) using two-step heat treatments. In example 2, the glass powder was heated at a rate of 20° C./min to 593° C. and held for 1 hour, wherein allows the nucleation of leucite; and then ramped to 833° C. and held for 1 hour hold. In example 2a, the glass powder was heated at a rate of 20° C./min to 606° C. and held for 1 hour, then ramped to 868° C. and held for 1 hour hold (Example 2a, FIG. 8). In example 2b, these temperatures comprised 613° C. for 1 hour hold and 903° C. for 1 hour. In example 2c, the heat treatments were 618° C. for 1 hour and 916° C. for 1 hour. Ramp rates were 20° C./min in both instances. After heat treatments the glass-ceramic were air quenched. All glass-ceramics were confirmed as tetragonal leucite according to XRD data.

Figure 9:
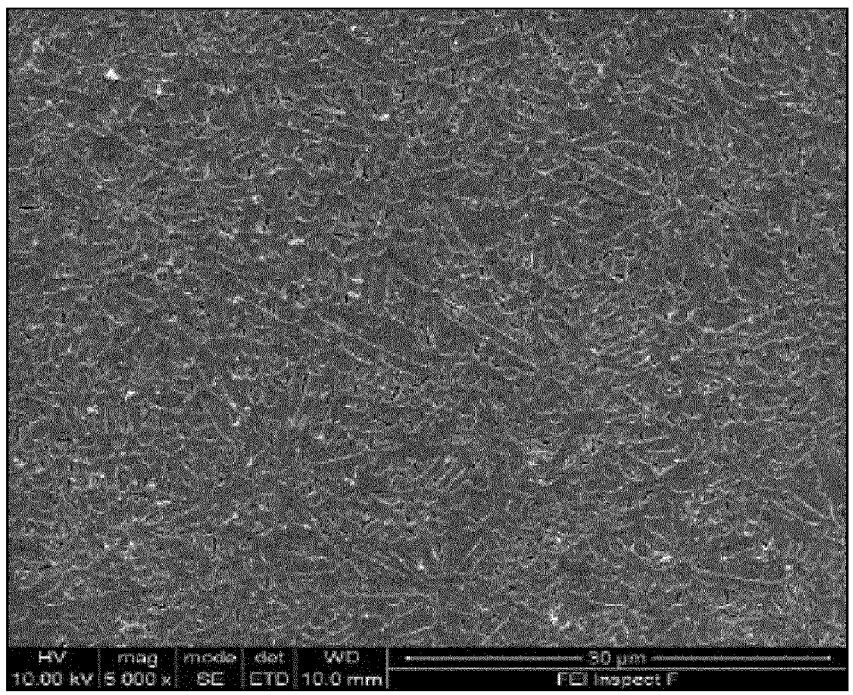
FIG. 9 shows the SEM photomicrograph of the glass-ceramic of Example 2b showing an increase of high aspect ratio leucite crystals in the glassy matrix.
Figure 10:
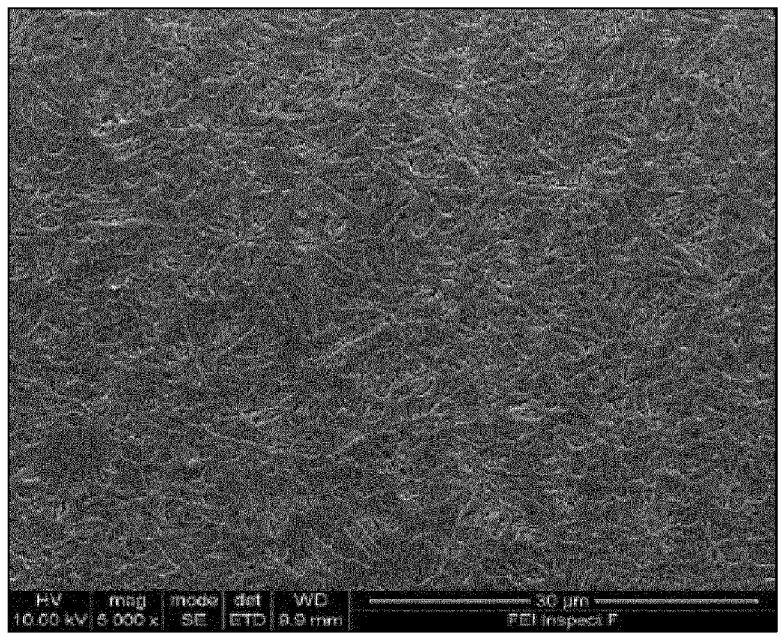
FIG. 10 shows the SEM photomicrograph of the glass-ceramic of Example 2c showing high aspect leucite crystals, with signs of cross-shaped geometry in the glassy matrix.
Figure 11:
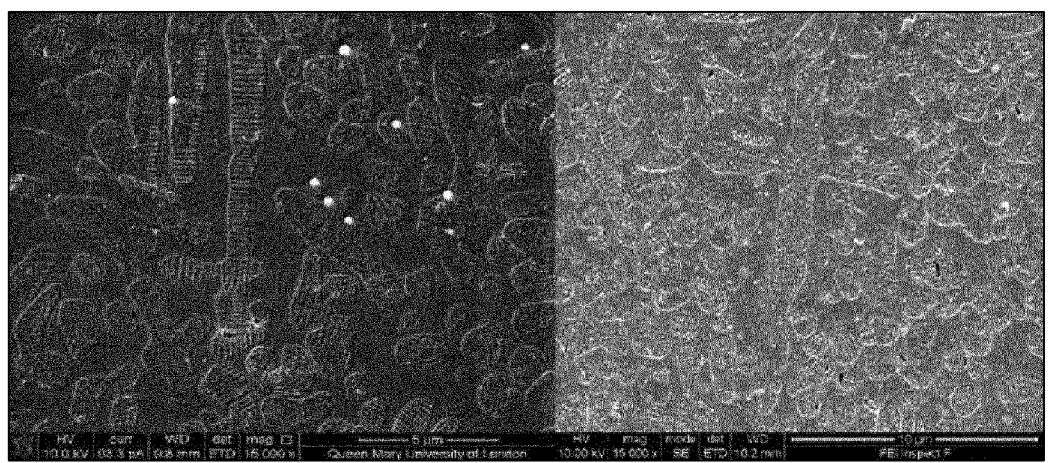
FIG. 11 shows the SEM photomicrograph of the glass-ceramic of Example 2c showing high aspect leucite crystals, with signs of cross-shaped geometry in the glassy matrix.

Example 2a (FIG. 8) demonstrates a largely uniform microstructure, with mostly rounded and few fiber like tetragonal leucite crystals present. Example 2b (FIG. 9) had an increasing fiber-like tetragonal leucite content with high aspect ratio and this was increased for example 2c, which also contained some cross shaped structures (FIGS. 10 and 11). There were no signs of microcracking in the glassy matrix and microcracking was restricted to the leucite crystals. The high TEC values (19.6 to 24.9×10−6/K at 100-400° C., Table III) confirm the high measured area fraction for these glass-ceramics (>54%). The controlled addition of increasing quantities of $TiO_2$ and CaO of equal molar %, and with $K_2O$ content kept at 12% and above, produced tetragonal leucite glass-ceramics with high reliability (m=9.4-18.9). Example 2a indicates a high Mean (SD) biaxial flexural strength of 224.9±24.9 MPa and reliability (m=10.9, Table III). These values are increased to a Mean (SD) of 234.8 (15.3) MPa and reliability (m=18.9) for example 2c with the increasing addition of $TiO_2$ and CaO (3%) of equal molar proportions and with $K_2O$ content kept at 12% and above (Table III). These values for reliability are higher than that found for traditional dental ceramics. Examples 2-2c demonstrate that the microstructure may be varied for these glass-ceramics from a high area fraction of more spherical crystals to those of a high aspect ratio with a resultant effect on the strength, toughness and reliability of the said glass-ceramics. Examples 2, 2a, 2b and 2c may be utilized as machineable or extrusion glass-ceramic materials for dental applications.

Example 3

Glass reagents batched in the form of silicates, carbonates and oxides consisted of the following components (Mole %):

Example 3

$SiO_2$, 69.3%; $Al_2O_3$, 10.1%; $K_2O$, 12.5%; CaO, 2.1%; $Nb_2O_5$, 0.5%; $Na_2O$, 3.9%; $LiO_2$, 1.1%; MgO, 0.5%.

Example 3a $SiO_2$, 69.3%; $Al_2O_3$, 10.1%; $K_2O$, 12.5%; CaO, 2.1%; $TiO_2$, 0.5%; $Nb_2O_5$, 0.5%; $Na_2O$, 4.0%; $LiO_2$, 1.1%; MgO, 0.5%.

The components were mixed on a jar roll for 2 hours. The batches were transferred to an 90% Pt-10% Rh crucible and heated in an electrical chamber furnace (UAF1600 furnace, Lenton, Hope Valley, UK) at a rate 10° C./min up to 1550° C. and held for 5 hours. The glass melt was next transferred into an annealing furnace (Tris Burnout furnace, Dentalfarm, Italy) operating at 500° C. for 2 hours, and then cooled down to room temperature. The glass frits were crushed and ground in a ball mill (Pascall Engineering ltd, UK) for 2 hours then screened using a 125 μm sieve. The glass powders were remelted for 2 hours at 1550° C., and annealed for 2 hours at 500° C. and furnace cooled to room temperature. Glasses were transparent. The glass frit was then re ground and sieved through a 125 micron sieve. All glasses prepared were transparent. X-ray diffraction was carried out on the glasses using a Siemens D5000 X-ray diffractometer using flat plate geometry. Graphite monochromated Cu Kα radiation ($\lambda 1$=1.54056 Å and $\lambda 2$=1.54439 Å) was used. Data was collected from 5 to 110° two-theta, with a step size 0.02° and a count time of 12 seconds. Glass samples were confirmed as amorphous.

Figure 12:
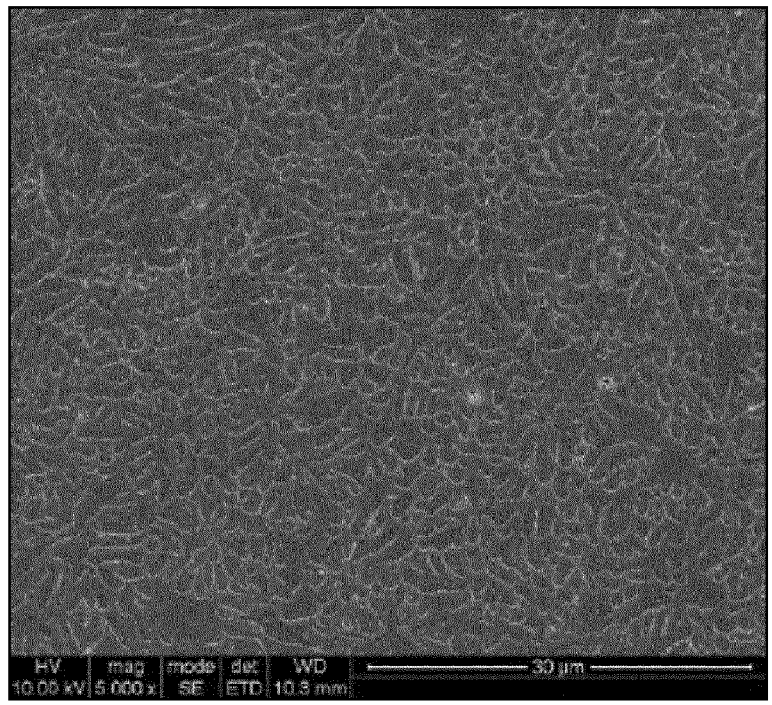
FIG. 12 shows the SEM photomicrograph of the glass-ceramic of Example 3 showing a high area fraction of leucite crystals in the glassy matrix.
Figure 13:
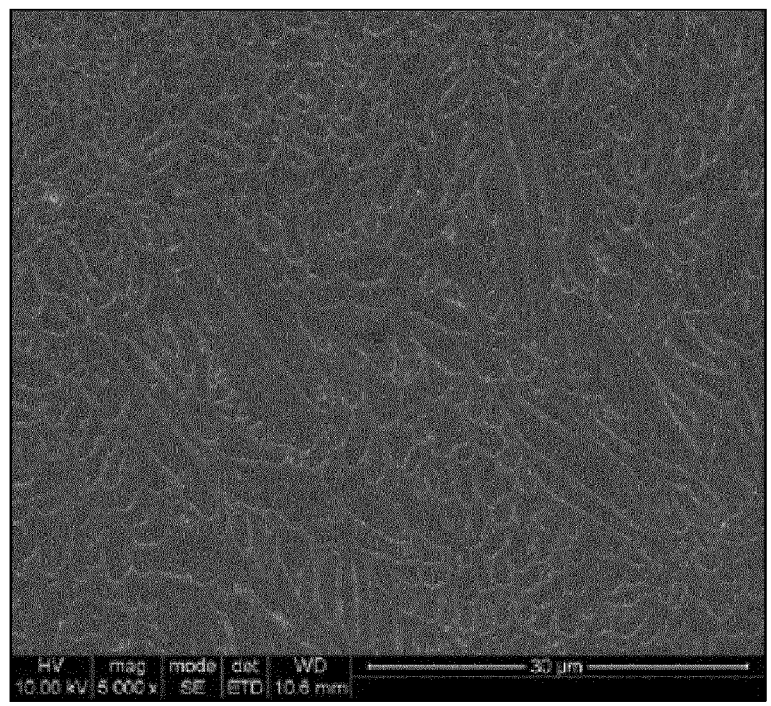
FIG. 13 shows the SEM photomicrograph of the glass-ceramic of Example 3a showing a high area fraction of leucite crystals with some high aspect ratio leucite crystallites.
Figure 14:
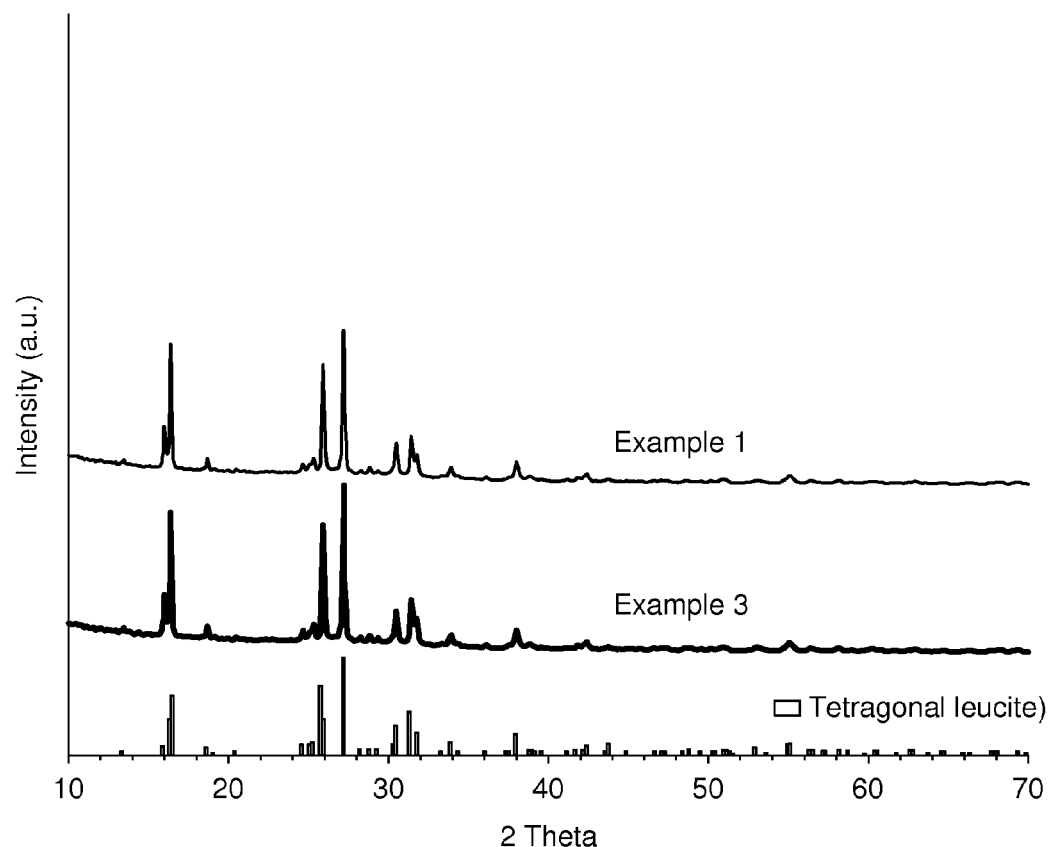
FIG. 14 shows the XRD plots for the glass-ceramic of Examples 1 and 3 demonstrating the presence of tetragonal leucite.

In order to crystallise the glass-ceramics, glass powders were heat treated in an electric furnace (RHF 1600, Carbolite, Bamford, UK) at 20° C./min to 630° C./1 hour and next ramped to 949° C./1 hour then air quenched (Example 3). A translucent glass-ceramic material was produced. For example 3a, the glasses were heated at 20° C./min to 620° C./1 hour and next ramped to 968° C./1 hour then air quenched. Glasses were ground and sieved through a 125 micron sieve. The heat treated glass-ceramics were confirmed as tetragonal leucite by the X-ray diffraction analysis. Using this crystallization process it was possible to demonstrate that a high area fraction (44.1%) of leucite crystals could be synthesized in the glass without the use of titanium dioxide as a nucleating agent (FIG. 12, 14). Titanium dioxide (0.5 mol %) was replaced by niobium oxide (0.5 mol %) in this example. It was previously thought that titanium dioxide needed to be present in the aluminosilicate glass composition to give the copious crystallization of leucite (Holland et al., 1995. J Non-Crystalline Solids 180; 292-307). Differential Scanning calorimetry (DSC) of different glass powder sizes (45, 125, 300 microns) for Example 3 indicated there was little difference in the peak crystallisation temperature (Tp) indicating a bulk crystallisation mechanism. FIG. 12 demonstrates that the microstructure was changed via this process when compared to Example 1 which contained titanium dioxide as a nucleating agent. Glass compositions with a mixed titanium dioxide (0.5 mole %) and niobium oxide content (0.5 mole %) were also produced and led to an increased aspect ratio of some of the leucite crystals (FIG. 13).

Example 4

Glass batches consisted of the following components (mole %):

Example 4

$SiO_2$, 69.7%; $Al_2O_3$, 10.6%; $K_2O$, 12.8%; CaO, 1.5%; $TiO_2$, 1.3%; $Na_2O$, 1.9%; $LiO_2$, 1.6%; $B_2O_3$, 0.7%.

Example 4a $SiO_2$, 69.2%; $Al_2O_3$, 10.5%; $K_2O$, 12.7%; CaO, 1.22%; $TiO_2$, 0.94%; $Na_2O$, 1.87%; $LiO_2$, 3.0%; $B_2O_3$, 0.7%.

Example 4b $SiO_2$, 68.4%; $Al_2O_3$, 10.4%; $K_2O$, 12.5%; CaO, 1.2%; $TiO_2$, 0.93%; $Na_2O$, 1.85%; $LiO_2$, 4.0%; $B_2O_3$, 0.7%.

The components were mixed on a jar roll for 2 hours. The batch was transferred to a 90% Pt-10% Rh crucible and heated in an electrical chamber furnace (UAF1600 furnace, Lenton, Hope Valley, UK) at a rate 10° C./min up to 1550° C. and held for 6 hours (or heated up to 1520° C. and held for 5 hours for example 4a). The glass melt was transferred into an annealing furnace (Tris Burnout furnace, Dentalfarm, Italy) operating at 500° C. for 1 hour, then cooled to room temperature. Glasses were then crushed and ground to a powder for 2 hours and then remelted for 2 hours at 1550° C. followed by annealing for 2 hours at 500° C. and furnace cooling to room temperature. The glass frit was then re ground and sieved through a 125 micron sieve. All glasses prepared were transparent. X-ray diffraction was carried out on the glasses using a Siemens D5000 X-ray diffractometer using flat plate geometry. Graphite monochromated Cu Kα radiation ($\lambda 1$=1.54056 Å and $\lambda 2$=1.54439 Å) was used. Data were collected from 5 to 110° two-theta, with a step size 0.02° and a count time of 12 seconds. Glass samples were confirmed as amorphous and leucite free.

Figure 15:
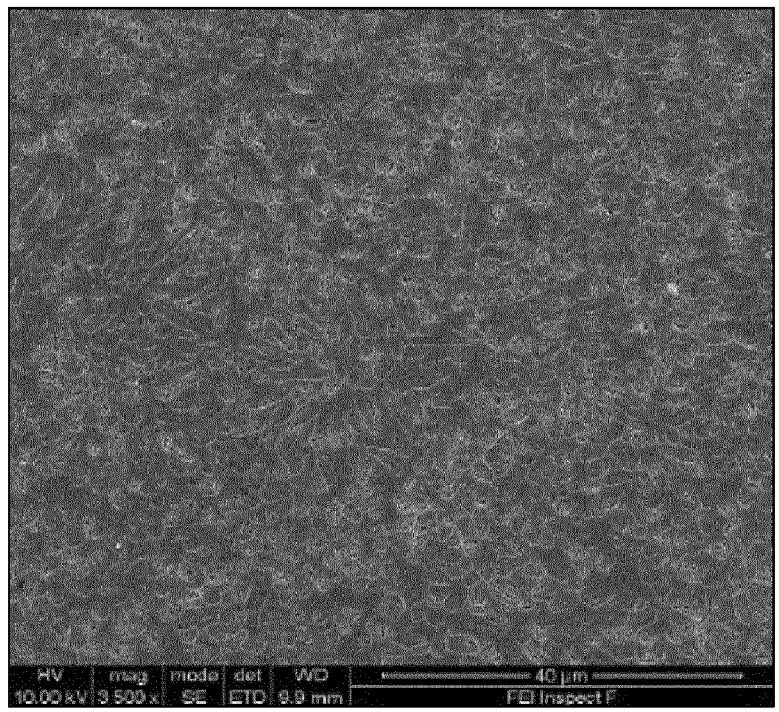
FIG. 15 shows the SEM photomicrograph of the glass-ceramic of Example 4 showing a high area fraction of leucite crystals with some elongated leucite crystallites.
Figure 16:
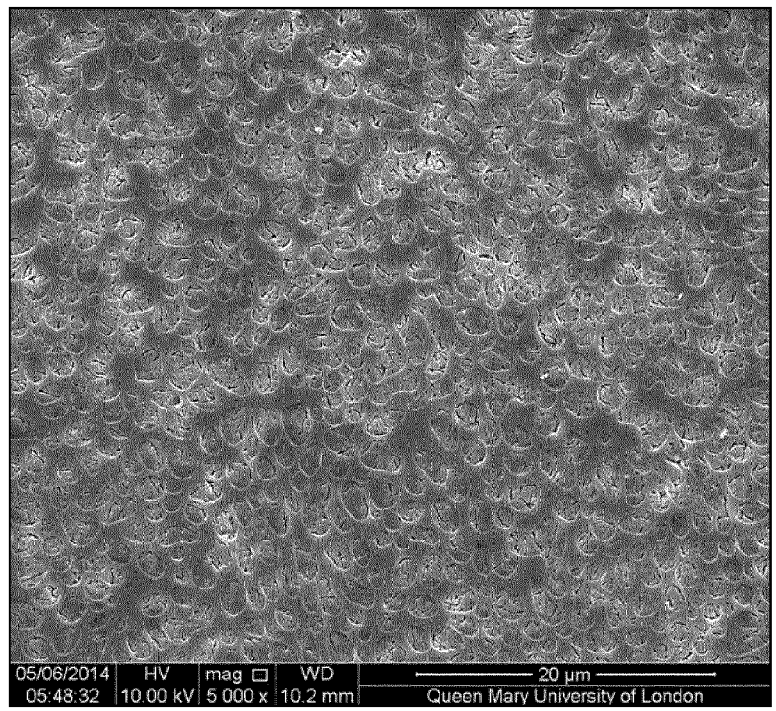
FIG. 16 shows the SEM photomicrograph of the glass-ceramic of Example 4a showing a high area fraction of spherical leucite crystals uniformly distributed in the glassy matrix.

In order to crystallise the glass-ceramics, glass powder was heat treated in an electric furnace (RHF 1600, Carbolite, Bamford, UK) at 10° C./min to 618° C./1 hour and next ramped to 1040° C./1 hour (for Example 4) then air quenched. Alternatively (for Example 4a), glass powder was heat treated at 10° C./min to 596° C./1 hour and next ramped to 1040° C./30 mins then air quenched. Glasses were ground and sieved through a 125 micron sieve. The heat treated glass-ceramics were confirmed as tetragonal leucite by the XRD analysis. A mixture of rounded and elongated tetragonal leucite crystals (>54%) dispersed in glassy matrix was crystallised (FIGS. 15, 16). This translucent tetragonal leucite glass-ceramic resulted in a high biaxial flexural strength 229.7 (40.4) MPa (Table III).

Figure 17:
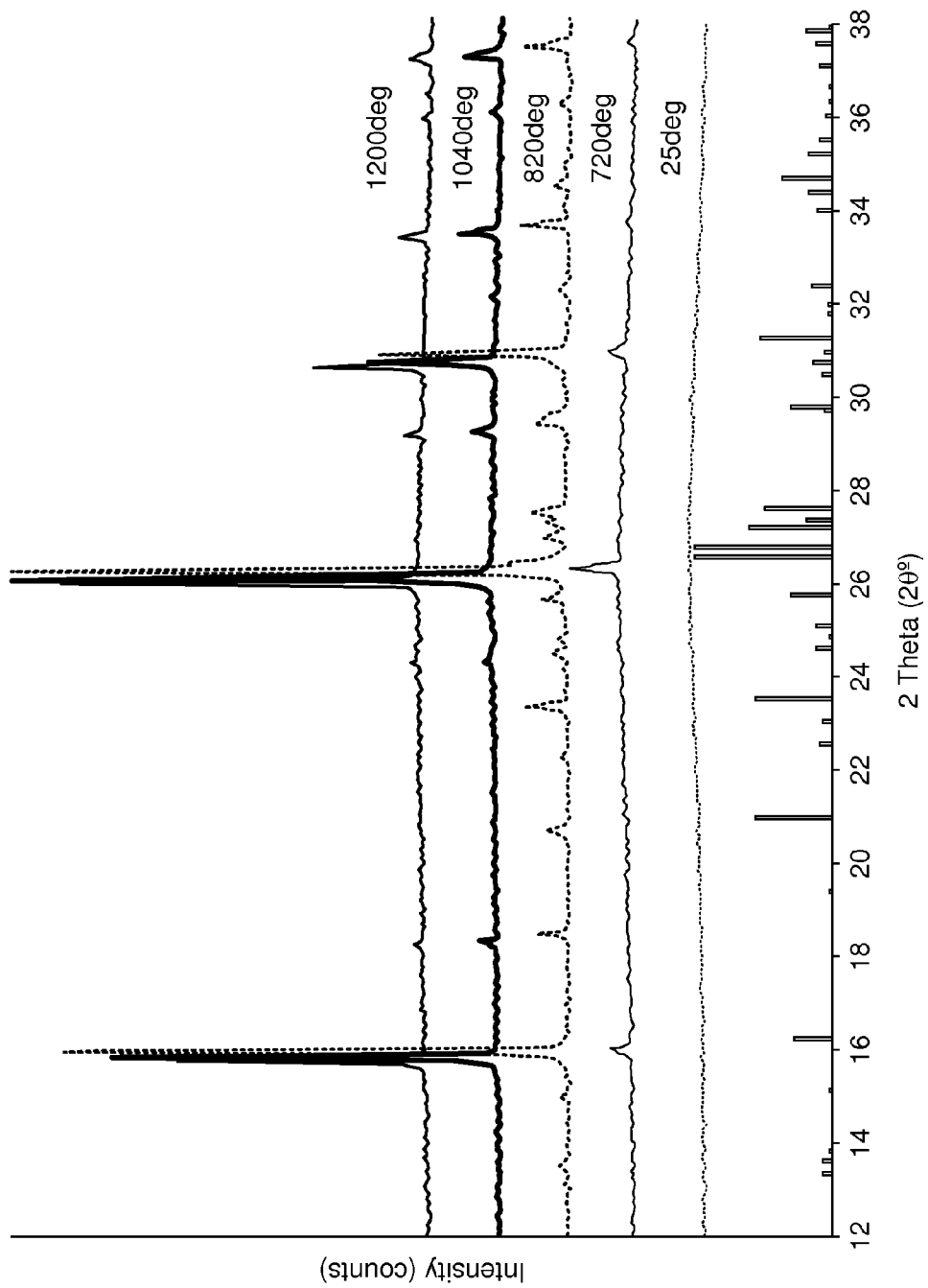
FIG. 17 shows the high temperature XRD patterns for the glass-ceramic of Example 4 indicating the presence of sanidine and leucite at different crystallisation temperatures.
Figure 18:
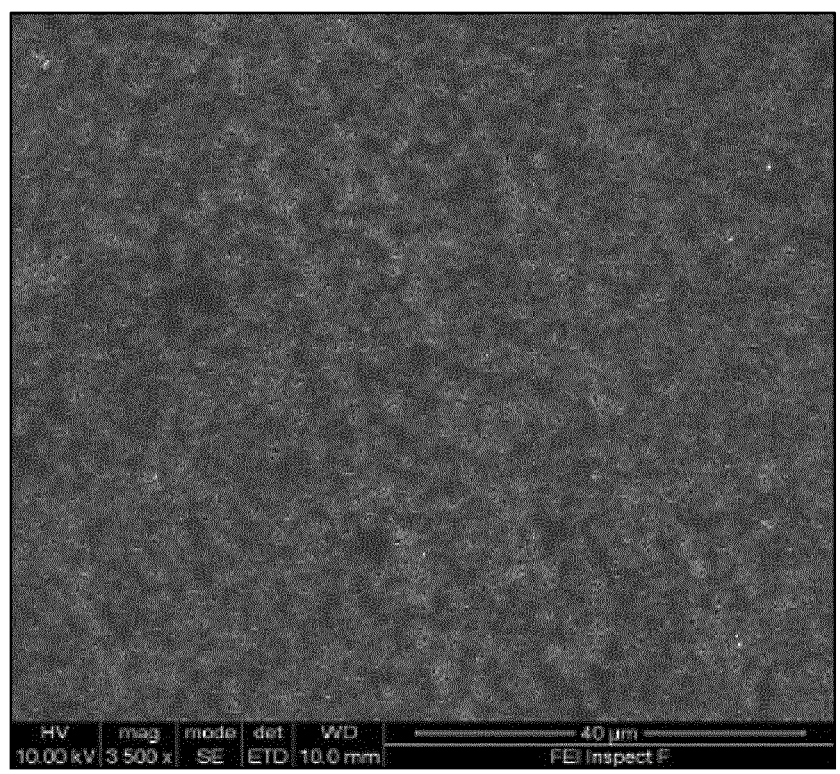
FIG. 18 shows the SEM photomicrograph of the glass-ceramic of Example 4 showing a high area fraction of fine spherical leucite crystals uniformly distributed in the glassy matrix.

High temperature XRD of Example 4 also confirmed it was possible to crystallize (820-1075° C.) a sanidine phase or a mixed leucite-sanidine phase in this glass composition (FIG. 17). High temperature XRD of Example 4a also indicates the presence of sanidine from 750-1000° C. It is possible to crystallize tetragonal leucite/sanidine or a mixed phase leucite-sanidine glass-ceramic in this composition by changes to the crystallization temperatures. The said mixed phase leucite-sanidine glass-ceramic or sanidine glass-ceramic is claimed in this disclosure as the lower thermal expansion characteristics of these glass-ceramics may make them useful as stronger veneering materials for zirconia, alumina or metallic substrates. In order to study surface crystallization effects, the glass powder was also prepared using high speed planetary milling (Pulverisette P7, Fritsch, Idar-Oberstein, Germany) at 1000 rpm for 30 minutes, followed by freeze drying the powder to avoid particle agglomeration. It was possible to crystallize a high area fraction (55.9%) of spherical crystallites uniformly distributed in the glassy matrix using the previous crystallisation parameters (FIG. 18). This material should produce low wear with the tooth enamel according to previous work (Theocharopoulos et al., J Dent Res, 2012; 91, Spec Iss C:29) and sufficient strength as an all-ceramic veneer material.

Examples 5 and 6

Glass reagents batched in the form of silicates, carbonates and oxides consisted of the following components (Mole %):

Example 5

$SiO_2$, 70.9%; $Al_2O_3$, 10.0%; $K_2O$, 10.9%; CaO, 2.1%; $TiO_2$, 0.5%; $Na_2O$, 3.9%; $LiO_2$, 1.1%; MgO, 0.5%.

Example 6

$SiO_2$, 71.9%; $Al_2O_3$, 10.1%; $K_2O$, 9.5%; CaO, 2.0%; $TiO_2$, 2.2%; $Na_2O$, 2.6%; $LiO_2$, 1.1%; MgO, 0.5%.

Figure 19:
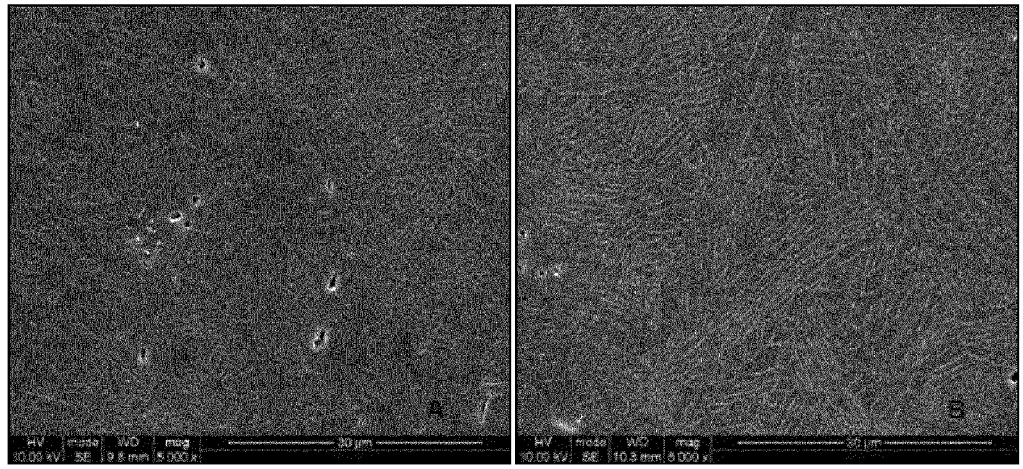
FIG. 19 shows a first SEM image of the leucite glass-ceramic of Example 5 and a second SEM image of the leucite glass-ceramic of Example 5 after 620/2 hr and 920/1 hr holds.

The components were mixed on a jar roll for 2 hours and transferred to an alumina crucible (CC68, Almath Crucibles Ltd, UK), and heated in an electrical chamber furnace (UAF1600 furnace, Lenton, UK) at a rate of 10° C./min to 1550° C. and held for 5 hours. The molten glass was immediately transferred to a preheated annealing furnace (Tris Burnout furnace, Dentalfarm, Italy) and annealed at 500° C. for 2 hours, followed by furnace cooling. The glass frits were crushed and ground in a ball mill (Pascall Engineering ltd, UK) for 2 hours then screened using a 125 μm sieve. In order to produce leucite glass-ceramics the glass was heated using a two-step heat treatment. In one embodiment, the glass was heated at a rate of 10° C./min to 620° C. for a 1 hour hold, then ramped to 920° C. for a 1 hour hold (Example 5, FIG. 19a). A refinement of this leucite microstructure was noticed on extending the nucleation hold to 2 hours (FIG. 19b). It was possible to produce sanidine or leucite/sanidine glass-ceramics by heat treating the said glass in the temperature range of 720-880° C.

For Example 6, the glass was heated at 10° C./min to 670° C. and held for 1 hour and next ramped to 1000° C. and held for 1 hour. After the heat treatment, the glass-ceramic was air quenched and then ground and sieved through a 125 micron sieve. Tetragonal leucite was the only phase detected in both examples 5 and 6. Example 5 illustrates a leucite glass-ceramic with a mixed morphology of both spherical and fiber-like crystals interspersed in the glassy matrix. Domains of orientated fibers are in evidence (FIG. 19b). It was possible to alter the microstructure by the application of a higher crystal growth temperature (960° C.) to produce a more spherical leucite morphology. Some minor areas with a dense dispersal of rod like structures were also present. The glass-ceramic produced was translucent (refractive index=1.507).

Figure 20:
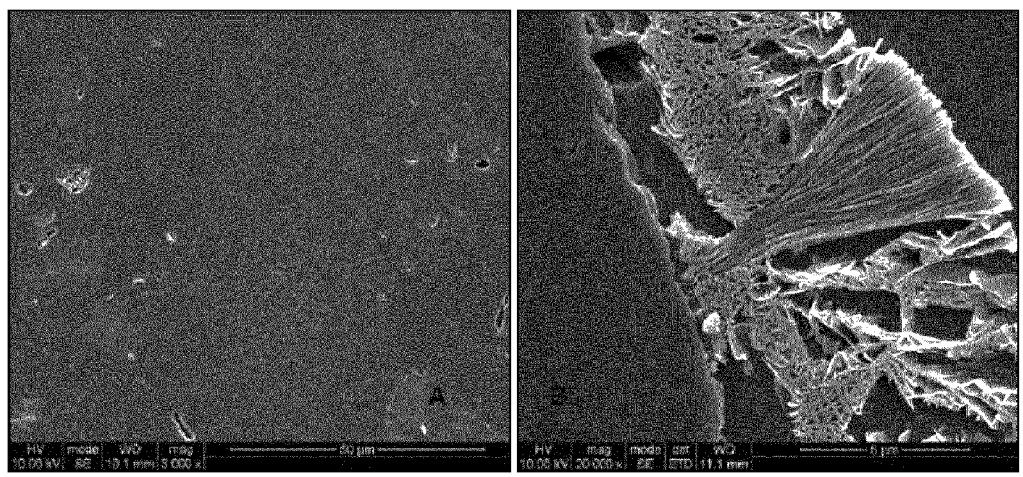
FIG. 20 shows two SEM images of the glass-ceramic frit of Example 6.

Example 6 produced a glass-ceramic which was opaque (refractive index=1.560). Leucite crystal coalescence and large areas of glassy matrix are in evidence (FIG. 20a) compared with Examples 1 and 2. Microcracking is present in the microstructure. The said glass-ceramic illustrated a lower leucite area fraction (33.1%) and this together with the glass and glass-ceramic thermal expansion coefficients (Tables II and III) were associated with the lower $K_2O$ content (33.1%). Glass and glass-ceramic microcracking was in evidence around large areas of crystallisation and this is reflected in the lower biaxial flexural strengths (Table IV). The increased Tg and Dsp in this glass might lead to stress relaxation due to the overlap of cubic/tetragonal leucite transformation temperature. Sparse areas of orientated fiber-like structures in bundles were observed within the microstructure (FIG. 20b) of high aspect ratio. Energy dispersive X-ray analysis revealed these fibers were aluminium and potassium rich compared to the surrounding leucite crystals.

Examples 7 and 8

Glass reagents batched in the form of silicates, carbonates and oxides consisted of the following components (Mole %):

Example 7

$SiO_2$, 70.6%; $Al_2O_3$, 8.5%; $K_2O$, 12.7%; CaO, 2.1%; $TiO_2$, 0.5%; $Na_2O$, 4.0%; $LiO_2$, 1.1%; MgO, 0.5%.

Example 8

$SiO_2$, 71.0%; $Al_2O_3$, 8.6%; $K_2O$, 12.8%; CaO, 1.0%; $TiO_2$, 1.0%; $Na_2O$, 4.0%; $LiO_2$, 1.1%; MgO, 0.5%.

The components were mixed on a jar roll for 2 hours. The batch was transferred to an 90% Pt-10% Rh crucible and heated in an electrical chamber furnace (UAF1600 furnace, Lenton, Hope Valley, UK) at a rate 10° C./min up to 1550° C. and held for 5 hours. The glass melt was next transferred into an annealing furnace (Tris Burnout furnace, Dentalfarm, Italy) operating at 500° C. for 1 hour, and then slowly cooled down to room temperature. The glass frits were crushed and ground in a ball mill (Pascall Engineering ltd, UK) for 2 hours then screened using a 125 μm sieve. The glass powders were re-homogenised by remelting for 2 hours at 1550° C., and annealed for 2 hours at 500° C. and furnace cooled to room temperature. The glass fit was then reground and sieved through a 125 micron sieve. All glasses prepared were transparent. X-ray diffraction was carried out on the glasses using a Siemens D5000 X-ray diffractometer using flat plate geometry. Graphite monochromated Cu Kα radiation (λ1=1.54056 Å and λ2=1.54439 Å) was used. Data were collected from 5 to 110° two-theta, with a step size 0.02° and a count time of 12 seconds. Glass samples were confirmed as amorphous.

Figure 21:
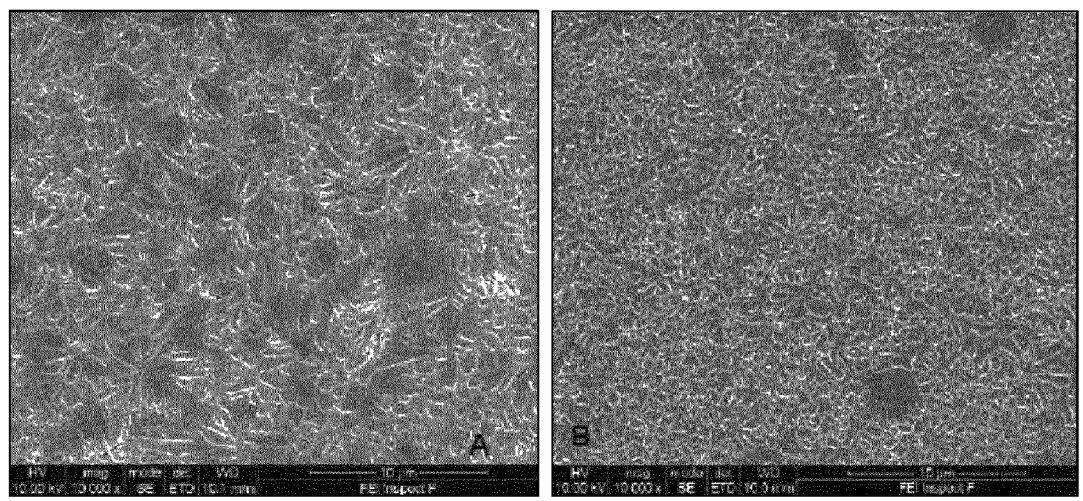
FIG. 21 shows a first SEM photomicrograph of the glass-ceramic of Example 7 and a second SEM photomicrograph of the glass-ceramic of Example 7 following a 30-minute high speed milling process showing the change in microstructure.

Glass-ceramics were produced by using two-step heat treatments of the glasses. In one embodiment, the glass was heated at a rate of 20° C./min to 588° C. for 1 hour hold, then ramped to 820° C. for a 1 hour hold (Example 7). For Example 8, the glass was heated at 20° C./min to 587° C. and held for 1 hour and next ramped to 931° C. and held for 1 hour. After the heat treatment, the glass-ceramics were air quenched and then ground and sieved through a 125 micron sieve. Tetragonal leucite was the only phase detected in Example 7 (FIG. 21) and in Example 8. Reduction in $Al_2O_3$ content in a series of glasses led to reductions in biaxial flexural strength (Table IV). In Example 7a (Table IV) recovery in biaxial flexural strength (204.7 MPa) was possible via high speed ball milling (0.5 hrs) (Pulverisette P7, Fritsch, Idar-Oberstein, Germany) at 1000 rpm and freeze drying the glass (0.5 hrs) before crystallization heat treatments. A fine (<0.5 microns) leucite crystal microstructure was also achieved via this surface crystallization process (FIG. 21).

Example 9

Determination of Physical Properties of Leucite Glass-Ceramics

A) Thermal Expansion Coefficient

Experimental glass and glass-ceramics frits were cut into blocks (6×6×16 mm) using a diamond saw. The thermal expansion coefficient (TEC) of the glass and glass-ceramics were measured using a differential dilatometer (DIL 402PC, Netzsch Instrument, Germany) in a temperature range of between 20° C. and 1200° C. at a heating rate of 3° C./min with softening point protect. The expansion coefficient was determined in the range of 100-400° C. and between 400-600° C. The results of these experiments indicated a good correlation between the Appen glass predictions and measured TEC of the glasses (Table II).

TABLE II

Results of the differential dilatometry for the experimental glasses.

| | TEC (×10⁻⁶/K, 100-400° C.) | | | |
|---|---|---|---|---|
| Glass | Predicted | Measured | $T_g$ (° C.) | $D_{sp}$ (° C.) |
| Example 1 | 10.3 | 10.4 | 581.0 | 676.2 |
| Example 1a | | 10.0 | 589.7 | 669.9 |
| Example 2 | 10.3 | 10.3 | 562.5 | 667.5 |
| Example 2a | 10.3 | 9.9 | 578.2 | 671.5 |
| Example 2b | 10.3 | 10.0 | 582.7 | 675.3 |
| Example 2c | 10.4 | 9.98 | 596.1 | 657.4 |
| Example 3 | — | 9.7 | 593.1 | 671.6 |
| Example 3a | — | 9.8 | 587.0 | 667.4 |
| Example 4 | 9.7 | 9.01 | 679.0 | 584.0 |
| Example 4a | 9.96 | 9.5 | 566.0 | 654.6 |
| Example 5 | 9.7 | 9.8 | 590.3 | 667.9 |
| Example 6 | 8.7 | 8.7 | 639.3 | 727.1 |
| Example 7 | 10.55 | 10.5 | 639 | 558.0 |
| Example 8 | 10.53 | 10.7 | 553.9 | 637.6 |

TABLE III

Results of the differential dilatometry for the experimental glass-ceramics.

| Glass-ceramic | TEC (×10⁻⁶/K, 100-400° C.) | Tg (° C.) | Dsp (° C.) |
|---|---|---|---|
| Example 1 | 19.7 | 478.3 | 619.8 |
| Example 1a | 21.0 | 480.8 | 608.9 |
| Example 2 | — | — | — |
| Example 2a | 20.23 | 471.7 | 611.8 |
| Example 2b | 19.61 | 486.8 | 657.1 |
| Example 2c | 24.87 | 508.7 | 658.5 |
| Example 3 | — | — | — |
| Example 3a | — | — | — |
| Example 4 | — | — | — |
| Example 5 | 18.6 | 579.7 | 675.8 |
| Example 6 | 15.7 | 627.2 | 736.5 |
| Example 7 | 18.72 | 462.2 | 583.6 |
| Example 8 | 19.01 | 410.5 | 613.1 |

B) Biaxial Flexural Strength

The flexural strength of glass-ceramics prepared in Examples 1 to 8 was tested using the biaxial flexural strength test. Glass-ceramic powders were compacted in a steel die and then transferred and sintered in a dental porcelain furnace. Test groups (n=30 per group) were tested by centrally loading the disc specimen on a 10 mm diameter knife-edge support with a 4 mm diameter spherical ball indenter. A thin plastic sheet (0.03 mm) was positioned between the specimen surface and the indenter to distribute the load evenly. The load was delivered by Instron testing machine (5567/H1580, Instron, Buckinghamshire, UK) at a crosshead speed of 1 mm/min until failure. The biaxial flexural strength was calculated using the following equation (Timoshenko and Woinowsky-Krieger, 1959):

$$\sigma_{max} = \frac{P}{h^2}\left\{(1+v)\left[0.485*\ln\left(\frac{a}{h}\right)+0.52\right]+0.48\right\}$$

Where $\sigma_{max}$ was the maximum tensile stress, P was the measured load at fracture, h was the specimen thickness, a was the radius of the knife-edge support and the Poisson's ratio v of 0.25.

TABLE IV

Results of the Biaxial flexural strength for the experimental glass-ceramics.

| Glass-ceramic | Biaxial Flexural Strength (MPa (SD) | m value | Characteristic strength σ₀ (MPa) | Glass-ceramic Colour |
|---|---|---|---|---|
| Example 1 | 199.3 (20.6) | 11.5 | 208.0 | Translucent |
| Example 1a | 212.3 (28.7) | 8.5 | 224.4 | Translucent |
| Example 1a (milled 2 hr) * | 192.5 (44.0) | 5.5 | 207.5 | Translucent |
| Example 1a (heat extruded) | 227 (35.2) | 7.3 | 241.8 | Translucent |
| Example 2a | 224.9 (24.9) | 10.9 | 235.6 | Translucent |
| Example 2b | 211.2 (26.7) | 9.4 | 222.5 | Translucent |
| Example 2c | 234.8 (15.3) | 18.9 | 241 | Whitish Translucent |
| Example 4 | 229.7 (40.4) | 6.7 | 245.7 | Translucent |
| Example 4a | 205.5 (35.3) | 6.7 | 220.2 | Translucent |
| Example 4 (milled 0.5 hrs)* | 168.7 | 7.9 | 179.1 | Translucent |
| Example 5 | 131.7 (9.0) | 17.6 | 135.6 | Translucent |
| Example 6 | 115.3 (10.2) | 13.2 | 119.7 | Opaque |
| Example 7 | 167.7 (28.8) | 6.8 | 179.5 | Translucent |
| Example 7 (milled 0.5 hrs)* | 204.7 (38.4) | 5.9 | 220.6 | Translucent |
| Example 8 | 158.4 (27.5) | 6.7 | 169. | Translucent |

*glass milled before nucleation and growth heat treatments

The invention claimed is:

1. A leucite glass-ceramic prepared from a glass comprising: 66.8 to 71.9 mol % of $SiO_2$, 8.5 to 10.6 mol % of $Al_2O_3$, 9.5 to 12.8 mol % of $K_2O$, 0.5 to 4.0 mol % of CaO, 0 to 3.0 mol % of $TiO_2$, 1.8 to 4.0 mol % of $Na_2O$, 0.1 to 6.0 mol % of $Li_2O$, 0 to 1.0 mol % of MgO, 0 to 3.0 mol % of $Nb_2O_5$, and 0 to 3.0 mol % of $B_2O_3$.

2. A leucite glass-ceramic according to claim 1, wherein the leucite glass-ceramic is prepared from a glass comprising: 66.8 to 71.9 mol % of $SiO_2$, 8.5 to 10.3 mol % of $Al_2O_3$, 9.5 to 12.8 mol % of $K_2O$, 0.5 to 4.0 mol % of CaO, 0 to 3.0 mol % of $TiO_2$, 1.9 to 4.0 mol % of $Na_2O$, 0.1 to 2.0 mol % of $Li_2O$, 0 to 1.0 mol % of MgO, 0 to 3.0 mol % of $Nb_2O_5$, and 0 to 3.0 mol % of $B_2O_3$.

3. A leucite glass-ceramic according to claim 1, wherein the $K_2O$ content is from 10.0 to 12.8 mol %.

4. A leucite glass-ceramic according to claim 1, wherein the CaO content is from 0.5 to 3.0 mol %.

5. A leucite glass-ceramic according to claim 1, wherein the $TiO_2$ content is less than 0.1 mol %.

6. A leucite glass-ceramic according to claim 1, wherein the $Li_2O$ content is from 0.1 to 1.6 mol %.

7. A leucite glass-ceramic according to claim 1, wherein the MgO content is from 0 to 0.5 mol %.

8. A leucite glass-ceramic according to claim 1, wherein the $Nb_2O_5$ content is from 0.5 to 2.0 mol %.

9. A leucite glass-ceramic according to claim 1, wherein the $B_2O_3$ content is less than 0.1 mol %.

10. A leucite glass-ceramic according to claim 1, wherein the glass-ceramic is prepared from a glass comprising approximately equal molar percentages of CaO and $TiO_2$.

11. A leucite glass-ceramic according to claim 1, wherein the glass-ceramic displays high flexural strength of at least 200 MPa.

12. A leucite glass-ceramic according to claim 1, wherein the morphology of the crystals is mainly in the form of fibers, rosettes, and/or spheres.

13. A leucite glass-ceramic according to claim 1, wherein the glass-ceramic is translucent.

14. A leucite glass-ceramic according to claim 1, wherein the refractive index of the glass-ceramic and/or the thermal properties of the glass-ceramic are matched to the leucite phase.

15. A leucite glass-ceramic according to claim 1, wherein the glass-ceramic displays one or more of the following properties: (1) a leucite area fraction of from 33.1 to 65.7; (2) a glass coefficient of thermal expansion (CTE) of from $8.5\times10^{-6}$/K to $10.7\times10^{-6}$/K at 100-400° C.; and (3) a glass-ceramic coefficient of thermal expansion (CTE) of from $15.7\times10^{-6}$/K to $24.9\times10^{-6}$/K at 100-400° C.

16. A method of preparing a leucite glass-ceramic according to claim 1 comprising subjecting the glass to a nucleation heat treatment followed by a growth heat treatment.

17. A method of preparing a leucite glass-ceramic according to claim 1 comprising subjecting the glass to a nucleation heat treatment at a temperature of 587° C. to 670° C. for a duration of about 0.5 hours to 4 hours, followed by a growth heat treatment at a temperature of 795° C. to 1075° C. for a duration of 0.5 hours to 3 hours.

18. A method of preparing a leucite glass-ceramic according to claim 16, wherein:
   (a) the leucite glass-ceramic is crystallised via a bulk crystallisation mechanism, or
   (b) the leucite glass-ceramic is crystallised via a surface crystallisation mechanism.

19. A method of fabricating a Dental restoration comprising the leucite glass-ceramic according to claim 1, the method comprising one or more of the following processes: sintering, heat pressing, Computer-Aided Design/Computer-Aided Manufacturing (CAD/CAM) technology, and 3D printing technology.

20. The method of claim 19, wherein the Dental restoration is selected from the group consisting of: a ceramic Dental inlay, a crown, a veneer, a bridge, and a veneering material for a zirconium oxide restoration substrate, an alumina oxide restoration substrate, and a metal restoration substrate.

21. A Dental restoration selected from the group consisting of: a ceramic Dental inlay, a crown, a veneer, a bridge, and a veneering material for a zirconium oxide restoration substrate, an alumina oxide restoration substrate, and a metal restoration substrate, comprising a leucite glass-ceramic according to claim 1.

* * * * *